(12) United States Patent
Chung et al.

(10) Patent No.: US 10,626,145 B2
(45) Date of Patent: Apr. 21, 2020

(54) PEPTIDE WITH ANTI-OBESITY AND ANTI-DIABETES ACTIVITY AND USE THEREOF

(71) Applicant: CAREGEN CO., LTD., Anyang-si, Gyeonggi-do (KR)

(72) Inventors: Yong Ji Chung, Yongin-si (KR); Eun Mi Kim, Yongin-si (KR)

(73) Assignee: CAREGEN CO., LTD., Anyang-si, Gyeonggi-Do (KR)

( * ) Notice: Subject to any disclaimer, the term of this patent is extended or adjusted under 35 U.S.C. 154(b) by 0 days.

(21) Appl. No.: 16/359,645

(22) Filed: Mar. 20, 2019

(65) Prior Publication Data

US 2019/0270773 A1    Sep. 5, 2019

Related U.S. Application Data

(62) Division of application No. 15/569,322, filed as application No. PCT/KR2015/004749 on May 12, 2015, now Pat. No. 10,351,597.

(30) Foreign Application Priority Data

Apr. 28, 2015   (KR) ........................ 10-2015-0059648

(51) Int. Cl.
| | | |
|---|---|---|
| A61K 38/08 | (2019.01) | |
| C07K 7/06 | (2006.01) | |
| A61P 3/06 | (2006.01) | |
| A61P 3/00 | (2006.01) | |
| A61P 3/10 | (2006.01) | |
| A61K 38/22 | (2006.01) | |
| A61K 38/30 | (2006.01) | |
| A61P 3/04 | (2006.01) | |
| A61K 38/00 | (2006.01) | |

(52) U.S. Cl.
CPC ................ C07K 7/06 (2013.01); A61K 38/08 (2013.01); A61K 38/2264 (2013.01); A61K 38/30 (2013.01); A61P 3/00 (2018.01); A61P 3/04 (2018.01); A61P 3/06 (2018.01); A61P 3/10 (2018.01); A61K 38/00 (2013.01)

(58) Field of Classification Search
None
See application file for complete search history.

(56) References Cited

U.S. PATENT DOCUMENTS

| | | |
|---|---|---|
| 5,516,891 A | 5/1996 | Siwruk et al. |
| 6,087,334 A | 7/2000 | Beeley et al. |
| 6,310,040 B1 | 10/2001 | Bozyczko-Coyne et al. |
| 6,693,076 B1 | 2/2004 | Lewis et al. |
| 6,723,699 B1 | 4/2004 | Lewis et al. |
| 10,351,597 B2 | 7/2019 | Chung et al. |
| 2002/0132767 A1 | 9/2002 | Rosen et al. |
| 2004/0180386 A1 | 9/2004 | Carr et al. |
| 2007/0185025 A1 | 8/2007 | Palacios et al. |
| 2009/0169491 A1 | 7/2009 | Chung et al. |
| 2010/0278756 A1 | 11/2010 | Chung et al. |
| 2013/0344025 A1 | 12/2013 | Rosat |
| 2014/0018291 A1 | 1/2014 | Vignati et al. |
| 2016/0075739 A1 | 3/2016 | Chung et al. |
| 2018/0118783 A1 | 5/2018 | Chung et al. |
| 2019/0270772 A1 | 9/2019 | Chung et al. |
| 2019/0270773 A1 | 9/2019 | Chung et al. |
| 2019/0270774 A1 | 9/2019 | Chung et al. |

FOREIGN PATENT DOCUMENTS

| | | |
|---|---|---|
| CN | 110105432 A | 8/2019 |
| EP | 3290434 A1 | 3/2018 |
| JP | 7-500839 A | 1/1995 |
| JP | 2002-523424 A | 7/2002 |
| JP | 2018515471 A | 6/2018 |
| KR | 10-2007-0091568 A | 9/2007 |
| KR | 10-2014-0027594 A | 3/2014 |
| KR | 10-2014-0134083 A | 11/2014 |
| WO | 93/08826 A1 | 5/1993 |
| WO | 94/04569 A1 | 3/1994 |
| WO | 02/069232 A2 | 9/2002 |
| WO | 03/062275 A1 | 7/2003 |
| WO | 2007/087468 A2 | 8/2007 |
| WO | 2007/102686 A1 | 9/2007 |
| WO | 2007/141309 A2 | 12/2007 |
| WO | 2014/052451 A2 | 4/2014 |

(Continued)

OTHER PUBLICATIONS

NCBI sequence XP_031128866 for E3 ubiquitin ligase, downloaded Nov. 20, 2019.*
Office Action from New Zealand IP No. 737077, dated Feb. 18, 2019.
Guidance memo from Dec. 29, 2005.
Partial Supplementary European Search Report from European Appln. No. 15890803.8, dated Mar. 16, 2018.
International Search Report from PCT/KR2015/004749 (dated Sep. 21, 2015).
Merrifield "Solid Phase Peptide Synthesis. I. The Synthesis of a Tetrapeptide", J. Am. Chem. Soc., 85(14):2149-2154 (1963).
Florea, "Gene and alternative splicing annotation with AIR", Genome Research, 15(1):54-66 (2005).
Zini et al., "Partial sequencing and expression of genes involved in glucose metabolism in adipose tissues and skeletal muscle of healthy cats", Vet Journal, 180(1):66-70 (2009).

(Continued)

Primary Examiner — Fred H Reynolds
(74) Attorney, Agent, or Firm — Merchant & Gould P.C.

(57) ABSTRACT

A peptide and a peptide complex of the present invention exhibit an anti-obesity effect by inhibiting fat accumulation and decomposing already accumulated fat, and exhibit an excellent effect with respect to diabetes by effectively reducing blood sugar. The peptide and the peptide complex of the present invention decrease the expression of PPARγ, ACC, and aP2, which are adipogenic markers, increase the expression of pHSL, AMPK-α1, CGI-58, and ATGL, which are lipolytic factors, and reduce the size of fat cells and blood cholesterol values. The peptide and the peptide complex of the present invention, which have excellent activity and safety, can be advantageously applied to drugs and quasi-drugs.

10 Claims, 28 Drawing Sheets

Specification includes a Sequence Listing.

(56) References Cited

FOREIGN PATENT DOCUMENTS

| WO | 2014/185604 A1 | 11/2014 |
|---|---|---|
| WO | 2015/136108 A1 | 9/2015 |
| WO | 2016/175362 A1 | 11/2016 |

OTHER PUBLICATIONS

Extended European Search Report from European Appln. No. 15890803.8, dated Jul. 16, 2018.
Ujiie et al., "Identification of Amino-Terminal Region of Adiponectin as a Physiologically Functional Domain", Journal of Cellular Biochemistry, Wiley-Liss Inc. US., vol. 98, No. 1, May 1, 2006 (May 1, 2006), pp. 194-207.
Florea, Liliana ,et al., "Gene and alternative splicing annotation with AIR," 15:54-66, 2005 by Cold Spring Harbor Laboratory Press; ISSN 1088-9051/05, 13 pages.
Zini, Eric, et al., "Partial sequencing and expression of genes involved in glucose metabolism in adipose tissues and skeletal muscle of healthy cats," The Veterinary Journal 180 (2009) pp. 66-70, 5 pages.
English translation of Office Action issued in copending Columbian Patent Application 2017011998, dated May 31, 2019, previously cited in IDS filed Aug. 29, 2019.
Kodama, K. et al., "Insulin-like Growth Factor-1 (IGF-1)-derived Peptide Protects against Diabetes in NOD Mice." Autoimmunity, 37(6/7), 481-487 (2004).
Office Action issued in Colombian Patent application No. 2017011998 dated May 31, 2019.
Aguirre, G. A. et al, "Insulin-like growth factor-1 deficiency and metabolic syndrome." J. Translational Med. (2016) 14(3).
The webpage everyday magic, https://www.t1everydaymagic.com/type-1-and-type-2-diabetes-whats-the-difference/, available Oct. 2014.
NCBI reference sequence XP016874748, downloaded Nov. 21, 2019.
Yang, Wenya et al, "Economic cost of diabetes in the us in 2017." Diabetes Care (2018) 41 p. 917-928.
Office Action from U.S. Appl. No. 16/359,613, dated Dec. 4, 2019.
Office Action from U.S. Appl. No. 16/359,675, dated Dec. 4, 2019.
Zhao et al. "Insulin-like growth factor 1 promotes the proliferation and adipogenesis of orbital adipose-derived stromal cells in thyroid-associated ophthalmopathy," Experimental Eye Research, 107, 65-73 (2013).
Lewitt et al, "The Insulin-Like Growth Factor System in Obesity, Insulin Resistance and Type 2 Diabetes Mellitus." J Clin Med, vol. 3, No. 4, pp. 1561-1574 (2014).
Extended European Search Report from European Application No. 19199355.9, dated Jan. 24, 2020.
New Zealand First Examination Report from Application No. 747390, dated Nov. 21, 2019.
New Zealand First Examination Report from Application No. 747396, dated Nov. 21, 2019.
Boord et al., "Adipocyte Fatty Acid-Binding Protein, aP2, Alters Late Atherosclerotic Lesion Formation in Severe Hypercholesterolemia", Arterioscler Thromb Vasc biol., vol. 22, No. 10, 1686 (2002).
Canadian Examiner's Report (second Office Action) from Application No. 2,984,287, dated Nov. 7, 2019.
Okorokov Pavel Leonidovich, "Adipokines and specific chaperones in children obesity," Dissertation, Research Center for Endocrinology, Federal State Budgetary Institution of the Ministry of Health of the Russian Federation (2014).
Eurasian Office Action from Application No. 201792365128, dated Dec. 13, 2019.

* cited by examiner

| blood sugar level (mg/dL) | | | | | | | | |
|---|---|---|---|---|---|---|---|---|
| | | fasting blood sugar level | intake and diet | 30min post-meal | 60min post-meal | 120min post-meal | 240min post-meal | 300min post-meal |
| Normal | Normal | 105 | | 184 | 181 | 147 | 151 | 135 |
| high fat diabetes | PBS | 178 | | 227 | 250 | 301 | 247 | 200 |
| | peptide of SEQ ID NO: 1 | 172 | | 212 | 225 | 163 | 147 | 145 |

| blood sugar level (mg/dL) | | | | | | | | |
|---|---|---|---|---|---|---|---|---|
| | | fasting blood sugar level | intake and diet | 30min post-meal | 60min post-meal | 120min post-meal | 240min post-meal | 300min post-meal |
| Normal | Normal | 105 | | 184 | 181 | 147 | 151 | 135 |
| high fat diabetes | PBS | 178 | | 227 | 250 | 301 | 247 | 200 |
| | peptide of SEQ ID NO: 2 | 181 | | 219 | 231 | 174 | 158 | 152 |

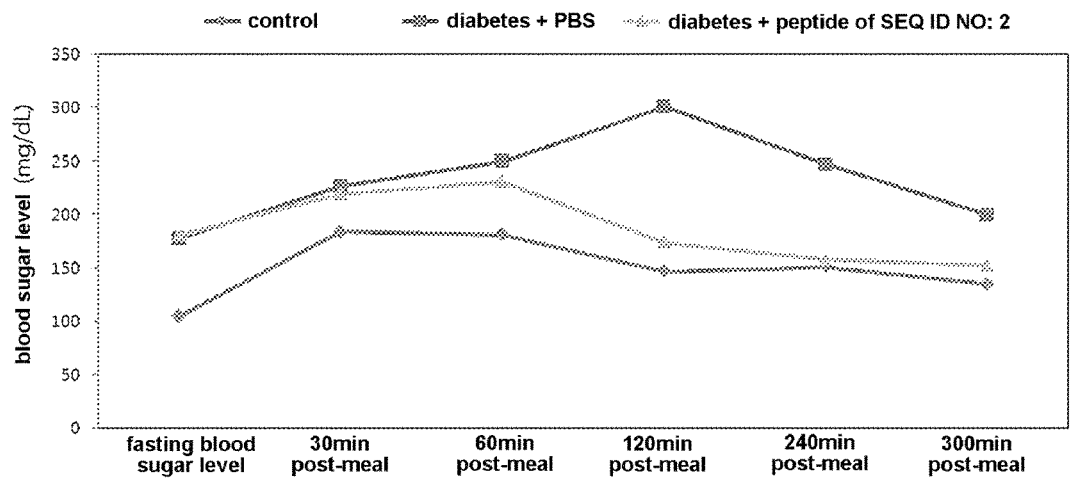

FIG. 22B

| blood sugar level (mg/dL) | | | | | | | | |
|---|---|---|---|---|---|---|---|---|
| | | fasting blood sugar level | intake and diet | 30min post-meal | 60min post-meal | 120min post-meal | 240min post-meal | 300min post-meal |
| Normal | Normal | 105 | | 184 | 181 | 147 | 151 | 135 |
| high fat diabetes | PBS | 178 | | 227 | 250 | 301 | 247 | 200 |
| | peptide of SEQ ID NO: 3 | 165 | | 220 | 231 | 198 | 172 | 166 |

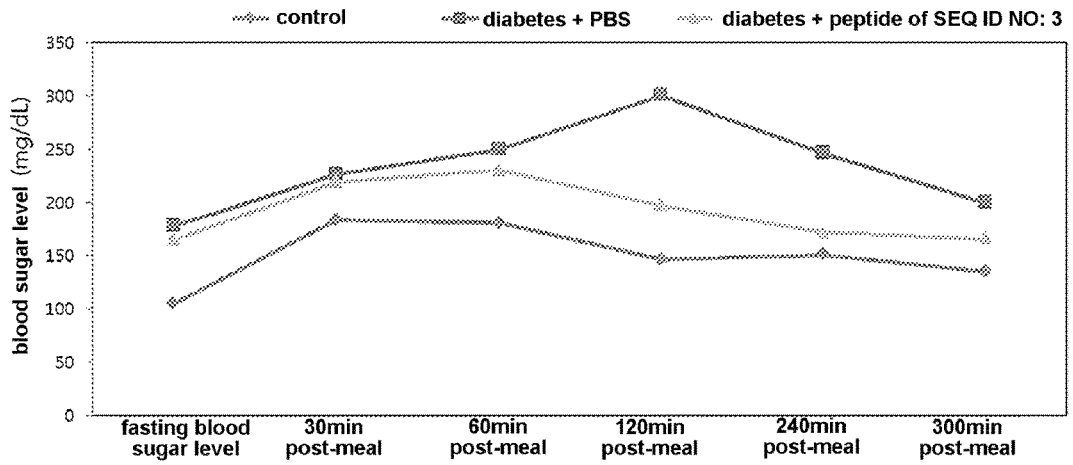

FIG. 22C

PEPTIDE WITH ANTI-OBESITY AND ANTI-DIABETES ACTIVITY AND USE THEREOF

TECHNICAL FIELD

This application is a divisional application of U.S. patent application Ser. No. 15/569,322 filed Oct. 25, 2017, which is a U.S. National Stage Application under 35 U.S.C. § 371 of International Patent Application No. PCT/KR2015/004749 filed May 12, 2015, which claims the benefit of priority to Korean Patent Application No. 10-2015-0059648, filed Apr. 28, 2015, to the KIPO. The disclosures of all of the above applications are hereby incorporated by reference in their entireties. The International Application was published in Korean on Nov. 3, 2016 as WO 2016/175362.

The present invention relates to a peptide with anti-obesity and anti-diabetes activity, and use thereof.

BACKGROUND

In Korea, dietary fat intake has recently increased with the growth of economy and the westernization of diet life, and onset of metabolic diseases such as obesity, diabetes, hyperlipidemia, hypertension, arteriosclerosis, and fatty liver increased due to insufficient exercise. In addition, obesity is an aesthetic problem to people who generally tend to prefer to slim body types as well as being associated with various disorders.

To date, therapeutic agents for obesity may be largely divided into drugs that act on the central nervous system to affect appetite and drugs that act on the gastrointestinal tract to inhibit uptake. Drugs acting on the central nervous system were placed on the market as anti-obesity drugs which work on the serotonin (5-HT) in the nervous system such as fenfluramine, dexfenfluramine and the like, on the noradrenaline nervous system such as ephedrine and caffeine, and on both the serotonin and the noradrenaline nervous system such as recently developed sibutramine, as classified by acting mechanisms. Representative of anti-obesity drugs acting on the gastrointestinal tract is orlistat, approved as a therapeutic agent for obesity, which inhibits intestinal lipase to reduce fat uptake. There are problems with some of the pre-existing drugs. For example, fenfluramine and the like have been prohibited from being marketed due to the side effect of incurring primary pulmonary hypertension or valvular heart disease, and other drugs cannot be applied to patients with heart failure or kidney failure due to the occurrence of blood pressure reduction or lactic acidosis.

Diabetes is a group of metabolic disorders caused when insulin is insufficiently secreted or in does that do not enable normal function (DeFronzo, 1988) and is characterized by hyperglycemia, that is, high blood sugar levels over a prolonged period, which causes various symptoms and syndromes, with glucose in urine. In recent years, the prevalence of obesity, particularly, abdominal obesity has increased, leading to the explosion of the prevalence of diabetes.

As of 2000, diabetes patients were estimated to be 170 million worldwide and expected to increase to 370 million people in 2030. However, a 2008 analysis report showed that the number of diabetes patients may have already reached 350 million worldwide (Danaei et al., 2011), with far more significant aggregation than expectation. It is reported that more than about 80% of type 1 diabetes patients are obese whereas only less than 10% of (non-)obese patients have diabetes (Harris et al. 1987). The correlation between diabetes and obesity is attributed to the fact that adipokines and free fatty acids are irregularly secreted to induce fatty acids to accumulate in insulin-sensitive tissues such as beta cells, kidneys, liver, heart, etc., resulting in lipotoxicity. If left without suitable treatment, chronic hyperglycemia may be prone to incurring various pathological symptoms including retinopathy, renal dysfunction, neuropathy, and vascular disorder. Indispensable for preventing such complications is effective blood sugar management.

Nowadays, the control of blood sugar levels is accomplished by lifestyle improvement (diet therapy, exercise therapy), and medications. However, diet therapy or exercise therapy is difficult to strictly manage and practice, with limitations of the effects thereof. Hence, most patients with diabetes rely on the control of blood sugar levels by medications such as insulin, insulin secretagogues, insulin sensitizer, and hypoglycemic agents, as well as lifestyle improvement.

Insulin produced using a recombinant method is used as a drug indispensable to type 1 diabetes patients and type 2 diabetes patients which fail to control blood sugar levels, and is advantageous in blood sugar control. However, it suffers from the disadvantage of repulsion to syringe needles, difficulty in administration, hypoglycemic risk, and weight gain.

Meglitinides, a kinds of insulin secretagogues, are short-acting agents and are taken before meals. Among them are NovoNorm (repaglinide), Fastic (nateglinide), and Glufast (mitiglinide). Insulin sensitizers are characterized by almost no hyperglycemic incurrence when taken alone, and may be exemplified by biguanide drugs, such as metformin, and thiazolidinedione drugs such as Avanida (rosiglitazone) and Actos (pioglitazone).

Recently, GLP-1 agonists have been developed using the action of glucagon-like peptide-1, which is an insulin secretion-stimulating hormone, and include exenatide and Victoza (liraglutide). In addition, DDP-4 inhibitors, which inhibit the action of DPP (dipeptidyl peptidase-4), an enzyme responsible for the rapid inactivation of GLP-1, are newly developed drugs and are representatively exemplified by Januvia (ingredient name: sitagliptin). However, those drugs are reported to have side effects of hepatoxicity, gastrointestinal disorders, cardiovascular disorders, and carcinogenicity. Another problem with the drugs is a high annual treatment cost, which is a barrier to the treatment of diabetes. Indeed, health care costs of pre-diabetes and diabetes approached about 200 trillion won in the USA as of 2007 (Dall et al., 2010), and health care costs of obesity are also near 150 trillion won only in the USA as of 2008 (Finkelstein et al., 2009). Therefore there is an urgent need for the development of a drug that can effectively lower blood glucose levels and can be applied to both diabetes and obesity-induced diabetes, with less side effects.

For this, the present inventors have recently paid attention to energy metabolism-regulating mechanisms in order to find an improved method for the treatment of obesity, and have made research of signals responsible for lipid accumulation and proteins affecting lipid accumulation upon the intake of high-fat diets in humans, with the premise that the compound to be developed should of higher safety (lower toxicity). As a result of research on signals for suppressing the expression of proteins responsible for fat accumulation and for degrading accumulated fat and on proteins involved in the signaling, the present inventors succeeded in developing peptides that promote lipolysis. In addition, the peptides of the present invention exhibit outstanding therapeutic efficacy on diabetes and obesity-induced diabetes. The fat accumulation induced by high-fat diets, the suppression of insulin signaling attributed to fat accumulation in the liver or muscle, and resulting insulin tolerance are causes of diabetes. Each and complexes of the peptides according to the present invention are therapeutically effective for such diabetes and obesity-induced diabetes.

Throughout this specification, reference is made to many papers and patent documents, with citations thereof indicated. The disclosures of the cited papers and patent documents are herein entirely incorporated by reference and thus the level of technical field to which the present invention belong and contents of the present invention are explained more definitely.

DETAILED DESCRIPTION OF THE INVENTION

Technical Problem

Culminating in the present invention, intensive and thorough research on the development of plural outstanding peptides having biologically effective activity, conducted by the present inventors, led to the finding that peptides having the amino acid sequences of SEQ ID NOS: 1 to 7 exhibit not only anti-obesity effects by suppressing high-fat diet-induced fat accumulation and degrading already accumulated fat, but also high therapeutic effects on diabetes and obesity-induced diabetes, and diabetes complications.

Accordingly, an object of the present invention is to provide peptides having the amino acid sequences of SEQ ID NOS: 1 to 7.

Another object of the present invention is to provide a peptide having anti-obesity or anti-diabetes activity.

A further object of the present invention is to provide a peptide complex having anti-obesity or anti-diabetes activity A still further object of the present invention is to provide a pharmaceutical composition for the prevention or treatment of obesity.

Still another object of the present invention to provide a pharmaceutical composition for the prevention or treatment of diabetes.

Other purposes and advantages of the present invention will become clarified by the following detailed description of the invention, claims, and drawings.

Technical Solution

One embodiment of the present invention provides a peptide having one selected from the group consisting of the amino acid sequences of SEQ ID NOS: 1 to 7.

Another embodiment of the present invention provides a peptide of anti-obesity and anti-diabetes activity having one selected from the group consisting of the amino acid sequences of SEQ ID NOS: 1 to 7.

Provided according to another embodiment of the present invention is a peptide complex of anti-obesity and anti-diabetes activity, composed of the following peptide combination:

(a) a peptide having the amino acid sequence of SEQ ID NO: 1;
(b) a peptide having the amino acid sequence of SEQ ID NO: 2 or 3; and
(c) a peptide having the amino acid sequence of SEQ ID NO: 6 or 7.

As a result of the effort of the present inventors to develop plural outstanding peptides having biologically effective activity, it was found that peptides having the amino acid sequences of SEQ ID NOS: 1 to 7 suppress high-fat diet-induced fat accumulation and degrade already accumulated fat, thus exhibiting an anti-obesity effect and a therapeutic effect on diabetes and obesity-induced diabetes, or diabetes complications.

As used herein, the term "peptide" refers to a linear molecule of amino acid residues linked by peptide bonds. The peptides of the present invention may be prepared using chemical synthesis methods known in the art, especially solid-phase synthesis techniques (Merrifield, J. Amer. Chem. Soc. 85:2149-54 (1963); Stewart, et al., Solid Phase Peptide Synthesis, 2nd. ed., Pierce Chem. Co.: Rockford, 111 (1984)) or a liquid-phase synthesis method (U.S. Pat. No. 5,516,891).

In order to select regions of the amino acid sequences thereof and increase the activity thereof, the peptides of the present invention may be modified at N- or C-terminals thereof. Through such modification, the peptides of the present invention may be imparted with a prolonged half-life after in vivo administration.

Further, C-terminals of the peptides of the present invention may be modified with a hydorxy group (—OH), an amino group (—NH2), an azide group (—NHNH2), etc. while N-terminals may be coupled with a protecting radical consisting of the group consisting of acetyl, fluorenyl methoxy carbonyl, formyl, palmitoyl, myristyl, stearyl, and polyethylene glycol (PEG). Through the above stated amino acid modification, the peptides of the present invention can greatly increase in stability. As used herein, the term "stability" is intended to refer to both in vivo stability and storage stability (e.g., stability during storage at room temperature). The protecting group acts to protect the peptides of the present invention against the attack of proteinases in vivo.

According to one embodiment of the present invention, the peptides of the present invention exhibit the effect of suppressing high-fat diet-induced fat accumulation and degrading already accumulated fat, decrease the expression of the adipogenic markers PPARγ, ACC, and aP2, increase the expression of the lipolytic factors pHSL, AMPK-α1, CGI-58, and ATGL, reduce the size of adipose cells, and lower blood cholesterol levels. These results indicate that the peptides of the present invention have excellent therapeutic effects on obesity, diabetes, and obesity-induced diabetes.

Not only individual peptides of SEQ ID NOS: 1 to 7, but also a complex thereof exhibits excellent anti-obesity and anti-diabetes activity.

According to the present invention, the peptides of SEQ ID NOS: 3, 5, and 7 correspond respectively to those of SEQ ID NOS: 2, 4, and 6, with the exception that the Cys residue is substituted with the Ser residue. The corresponding paired peptides are almost identical in terms of anti-obesity and anti-diabetes activity.

In accordance with an embodiment of the present invention, the peptide complex exhibiting anti-obesity or anti-diabetes activity is composed of a peptide having the amino acid sequence of SEQ ID NO: 1; a peptide having the amino acid sequence of SEQ ID NO: 2 or 3; and a peptide having the amino acid sequence of SEQ ID NO: 6 or 7.

According to another embodiment of the present invention, the peptide complex of the present invention is composed of peptides having the respectively amino acid sequences of SEQ ID NOS: 1, 3, and 7.

Contemplated in accordance with another aspect of the present invention is a pharmaceutical composition comprising the peptide or peptide complex of the present invention as an effective ingredient for preparing or treating obesity.

Superior in terms of anti-adipogenetic and lipolytic functions, the peptide or peptide complex of the present invention can be useful for the prophylaxis or therapy of obesity.

A further aspect of the present invention provides a pharmaceutical composition comprising the peptide or peptide complex of the present invention as an effective ingredient for preventing or treating diabetes.

Functioning to effectively lower an increased blood sugar level in diabetes animal models, the peptide or peptide complex of the present invention can find applications in the prophylaxis or therapy of diabetes.

According to some particular embodiments of the present invention, the composition of the present invention is a pharmaceutical composition comprising: (a) a pharmaceutically effective amount of the peptide or peptide complex of the present invention; and a pharmaceutically acceptable carrier. The term "pharmaceutically effective amount", as used herein, means a sufficient amount to achieve the above-stated efficacy or activity of the peptide.

The pharmaceutically acceptable carrier contained in the pharmaceutical composition of the present invention may be that commonly used in drug formulations and include, but are not limited to, lactose, dextrose, sucrose, sorbitol, mannitol, starch, acacia gum, calcium carbonate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. In addition to those ingredients, the pharmaceutical composition of the present invention may further comprise a lubricant, a humectant, a sweetener, a flavorant, an emulsifier, a suspending agent, and a preservative. With regard to pharmaceutically acceptable carriers and agents suitable for use, reference may be made to Remington's Pharmaceutical Sciences (19th ed., 1995).

The pharmaceutical composition of the present invention may be administered orally or parenterally. For parenteral administration, intramuscular, intravenous, subcutaneous, intraperitoneal, topical, or transcutaneous routes may be used.

The dosage of the pharmaceutical composition according to the present invention may vary depending on various factors, including dosage form, administration modality, the patient's age, weight, gender, state of health, diet, the time of administration, the route of administration, excretion rate, sensitivity, etc. For example, the pharmaceutical composition according to the present invention may be administered at a daily dose in the range of 0.0001 to 1,000 μg.

The pharmaceutical composition according to the present invention may be prepared in single-dose forms or in multi-dose packages using a pharmaceutically acceptable carrier and/or excipient according to a method that may be easily carried out by those skilled in the art. Herein, the formulation of the pharmaceutical composition may be a solution, suspension or emulsion of the pharmaceutical composition in oil or aqueous medium, or an extract, powder, granule, tablet or capsule containing the pharmaceutical composition, and may further comprise a dispersing agent or a stabilizer.

Advantageous Effects

Features and advantages of the present invention are summarized as follows:

(i) the peptides and the peptide complex of the present invention exhibit not only an anti-obesity effect by suppressing fat accumulation and degrading already accumulated fats, but also an outstanding therapeutic effect on diabetes by effectively reducing blood sugar levels.

(ii) the peptides and the peptide complex of the present invention decrease the expression of the adipogenic markers PPARγ, ACC, and aP2, increase the expression of the lipolytic factors pHSL, AMPK-α1, CGI-58, and ATGL, thus reducing adipocyte sizes and blood cholesterol levels.

(iii) the peptides and the peptide complex of the present invention have excellent activity and safety and thus can be advantageously applied to drugs and quasi-drugs.

BRIEF DESCRIPTION OF THE DRAWINGS

FIG. 22b shows changes in blood sugar level in obesity-induced DB/DB mouse models after treatment with the peptide of SEQ ID NO: 3.

FIG. 22c shows changes in blood sugar level in obesity-induced DB/DB mouse models after treatment with the peptide of SEQ ID NO: 5.

MODE FOR CARRYING OUT THE INVENTION

Figure 1A:
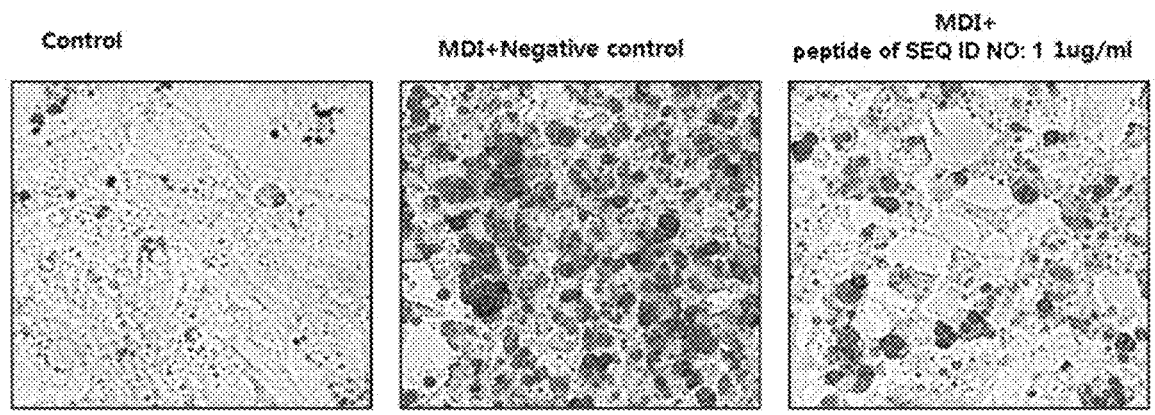
FIG. 1a shows lipids accumulated after treatment with peptides of the present invention, as analyzed by Oil red O staining the peptide of SEQ ID NO: 1.

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

EXAMPLES

Synthesis Example 1: Peptide Synthesis

In a reactor, 700 mg of chlorotrityl chloride resins (CTL resins, Nova biochem Cat No. 01-64-0021) was added with 10 ml of methylene chloride (MC) and stirred for 3 min. After removal of the solvent, 10 ml of dimethyl formamide (DMF) was added. The solution was stirred again for 3 min, and then the solvent was removed. To the reactor was added 10 ml of a dichloromethane solution, followed by 200 mmole of Fmoc-Asn(Trt)-OH (Bachem, Swiss) and 400 mmole of diisopropyl ethylamine (DIEA). The reactants were well dissolved and reacted while stirring for 1 hour. Thereafter, the solution was washed, and reacted with a solution of methanol and DIEA (2:1) in DCM (dichloromethane) for 10 min. Subsequent to washing with an excess of DCM/DMF (1:1), the solvent was removed. Then, 10 ml of dimethyl formamide (DMF) was added, followed by stirring for 3 min. After removal of the solvent, 10 ml of a deprotecting solution (20% piperidine/DMF) was added to the reactor. Stirring at room temperature for 10 min was precedent to the removal of the solvent. The deprotecting solution was added in the same amount and then removed after 10 min of reaction. Washing was performed twice with DMF, once with MC, and once with DMG for 3 min each wash to afford Asn-CTL resins. In another reactor, 200 mmole of Fmoc-Arg(Pbf)-OH (Bachem, Swiss), 200 mmole of HoBt, and 200 mmole of Bop were added to 10 ml of a DMF solution and well dissolved by stirring. To the reactor, 400 mmole of DIEA was added in two aliquots, followed by stirring for at least 5 min to the complete dissolution of the solid. The dissolved amino acid mixture solution was introduced into the reactor in which the deprotected resins were placed, followed by stirring for 1 hour at room temperature for reaction. After the reaction liquid was removed, stirring was carried three times for 3 min each time, together with a DMF solution which was then removed. A small amount of the reaction resins was taken and used in a Kaiser test (ninhydrin test) for examining an extent of the reaction. The same deprotection reaction was performed twice with the deprotecting solution to give Arg-Asn-CTL resins. The resins were sufficiently washed with DMF and MC before an additional Kaiser test. The following amino acid attachment experiments were carried out in the same manner as described above. According to selected amino acid sequences, reactions were sequentially induced with Fmoc-Thr(tBu)-OH, Fmoc-Lys(Boc)-OH, and Fmoc-Leu-OH in that order. The Fmoc-protecting group was removed by reacting twice with a deprotecting solution for 10 min for each reaction and then well washing. Acetic anhydride, DIEA, and HoBt were added and subjected to acetylation for 1 hour. The peptidyl resins thus obtained were washed with DMF, MC, and methanol three times each. The resins were dried with nitrogen gas slowly flowed and then were completely vacuum-dried under a P2O5 atmosphere. The resins were reacted for 2 hours at room temperature with 30 ml of a leaving solution (trifluoroacetic acid 81.5%, distilled water 5%, thioanisole 5%, phenol 5%, EDT 2.5%, and TIS 1%) while intermittently agitating. The resins were filtered and washed with a small volume of TFA solution, after which the filtrate was combined with the mother liquid. After distillation at a reduced pressure to reduce the total volume by two, 50 ml of cold ether was used to induce precipitation, and the precipitates thus formed were collected by centrifugation and washed twice with cold ether. After removal of the mother liquid, the remainder was sufficiently dried under a nitrogen atmosphere to afford 0.85 g of the unpurified peptide of SEQ ID NO: 1 NH2-Leu-Lys-Thr-Arg-Asn-COOH (yield: 92%). Synthesis was made of NH2-Lys-Gly-Ala-Cys(Ser)-Thr-Gly-Trp-Met-Ala-COOH in an amount of 0.78 g as peptides of SEQ ID NOS: 2 and 3 (yield: 82%), NH2-Ala-Cys(Ser)Thr-Leu-Pro-His-Pro-Trp-Phe-Cys(Ser)-COOH in an amount of 0.92 g as peptides of SEQ ID NOS: 4 and 5 (yield: 85%), and NH2-Cys(Ser)-Asp-Leu-Arg-Arg-Leu-Glu-Met-Tyr-Cys(Ser)-COOH in an amount of 0.76 g as peptides of SEQ ID NOS: 6 and 7 (yield: 88%). The peptides of SEQ ID NOS: 1, 2, 4, and 6 were found to have molecular weights of 630.7 (calc.: 630.7), 924.5 (calc.: 924.1), 1236 (calc.: 1236.5) and 1301.5 (calc.: 1301.5), respectively, as measured by mass spectrometry.

TABLE 1

| Peptide | Amino Acid Sequence | Analysis (Mass spectrometry) | |
|---|---|---|---|
| | | Measured | Calculated |
| SEQ ID NO: 1 | | 630.7 | 630.7 |
| SEQ ID NO: 2 | KGACTGWMA | 924.5 | 924.1 |
| SEQ ID NO: 3 | KGASTGWMA | | (908.0) |
| SEQ ID NO: 4 | ACYLPHPWFC | 1236 | 1236.5 |
| SEQ ID NO: 5 | ASYLPHPWFS | | (1269.4) |
| SEQ ID NO: 6 | CDLRRLEMYC | 1301.5 | 1301.5 |
| SEQ ID NO: 7 | SDLRRLEMYS | | |

Meanwhile, peptides of SEQ ID NOS: 1, 3, and 7 were mixed in equal amounts to give a peptide complex which was evaluated for efficacy.

Example 1: Assay for Inhibitory Activity Against Adipogenesis 1-1. Assay for Suppression of Lipid Accumulation by Use of Pre-Adipocyte (Oil Red O Staining)

The pre-adipocytes 3T3-L1 cells were grown to confluence and then incubated for two days with various concentrations of the peptides in a differentiation medium containing 10 μg/ml insulin, 0.1 μM dexamethasone, and 0.5 μM IBMX. The medium was exchanged every two days with a medium containing 10 μg/ml insulin. After differentiation was induced for 10 days, the generation of droplet in the cells was examined by Oil Red O staining. The prepared 3T3-L1 adipocytes were washed with PBS, fixed with 3.7% formalin for one hour, and washed with 60% isopropanol. The resulting cells were dyed with Oil Red O reagent at room temperature for 20 min. After removal of the Oil Red O reagent, the cells were washed three times with distilled water, and observed under a phase-contrast microscope. For quantitative analysis, fats were extracted from the cells using 100% isopropanol, and the cells were transferred in an amount of 200 μl/well into 96-well plates and measured for optical density at 500 nm using an ELISA reader.

Figure 1B:
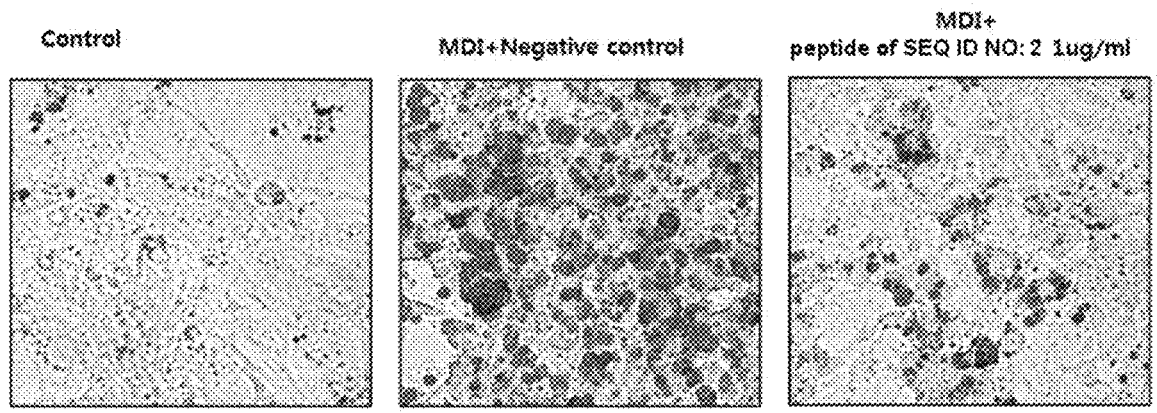
FIG. 1b shows lipids accumulated after treatment with peptides of the present invention, as analyzed by Oil red O staining the peptide of SEQ ID NO: 3.
Figure 1C:
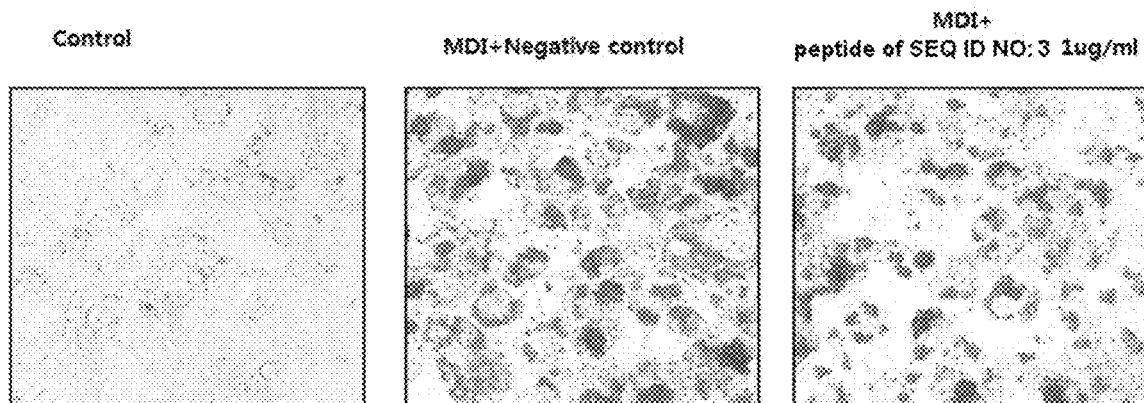
FIG. 1c shows lipids accumulated after treatment with peptides of the present invention, as analyzed by Oil red O staining the peptide of SEQ ID NO: 5.

Experimental data showed that treatment with peptides of SEQ ID NOS: 1, 3, and 5 decreased extents of fat accumulation in cells, as measured by Oil red O staining (FIGS. 1a-1c).

Figure 2:
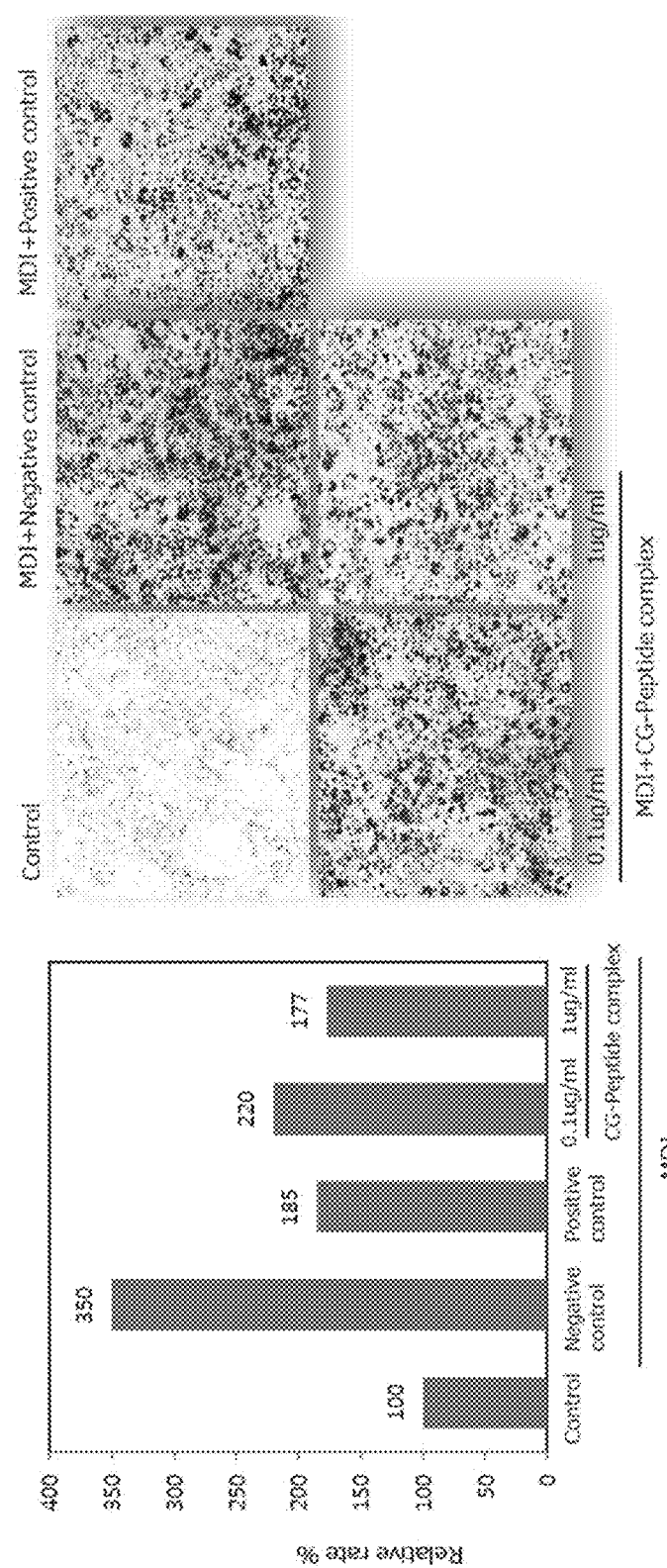
FIG. 2 shows results of lipid accumulation after treatment with the peptide complex of the present invention, as analyzed by Oil red O staining.

An extent of lipid accumulation in cells was also reduced when a complex of peptides of SEQ ID NOS: 1, 3, and 7 was applied by concentrations (FIG. 2).

1-2. Suppression of Expression of Genes Involved in Adipogenesis

3T3-L1 cells (pre-adipocytes) were seeded at a density of 3×105 cells/well into 6-well plates. After 24 hours of culturing, the cells were incubated at with predetermined concentrations (0.1, 1, and 10 μg/ml) of the peptides for 14 days in a 37° C. incubator. Thereafter, the cells were harvested and treated with an RNA extraction solution (Easy Blue, Intron) to prepare RNA from which cDNA was then synthesized using an RT premix (Intron). PCR was performed using primers for antigenic markers (PPARγ, ACC, and aP2), and a PCR premix (Intron).

Target-specific primer sequences for PCR of adipogenic markers were as follows: PPARγ forward primer sequence, 5'-TTTTCAAGGGTGCCAGTTTC-3' and PPARγ reverse primer, 5'-AATCCTTGGCCCTCTGAGAT-3' (annealing temperature, 60° C.); ACC forward primer sequence, 5'-AC- CTTACTGCCATCCCATGTGCTA-3' and ACC reverse primer, 5'-GTGCCTGATGATCGCACGAACAAA-3' (annealing temperature, 60° C.); aP2 forward primer sequence, 5'-CATCAGCGTAAATGGGGATT-3' and aP2 reverse primer, 5'-ACACATTCCACCACCAGCTT-3' (annealing temperature, 60° C.)

PCR products were each loaded in a volume of 5 μl into a 1% agarose gel, and electrophoresed, followed by identifying bands in a Gel-Doc.

Figure 3A:
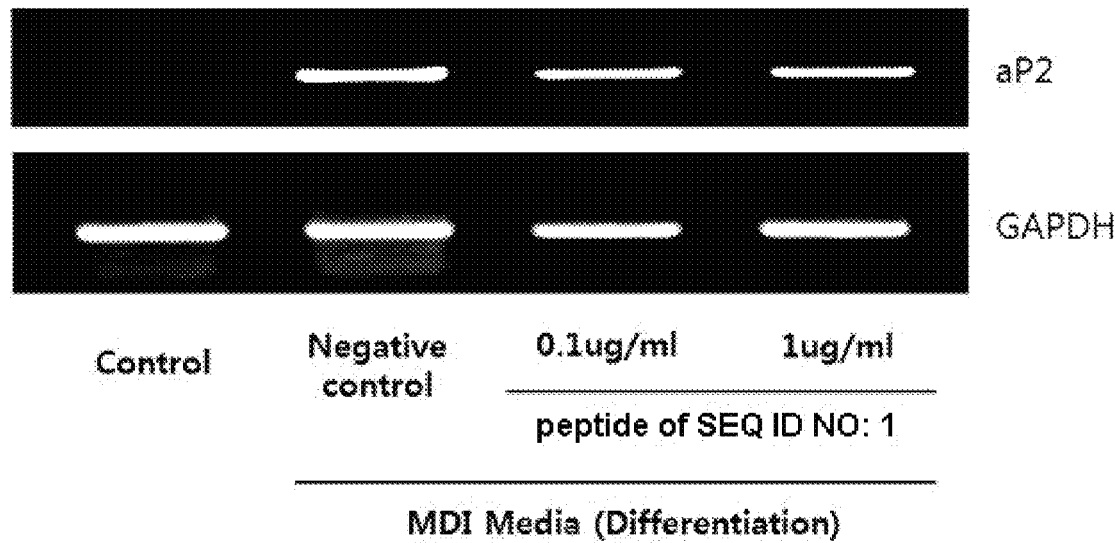
FIG. 3a shows measurement results of the expression levels of the gene aP2, which is involved in adipogenesis, after treatment with the peptide of SEQ ID NO: 1.
Figure 3B:
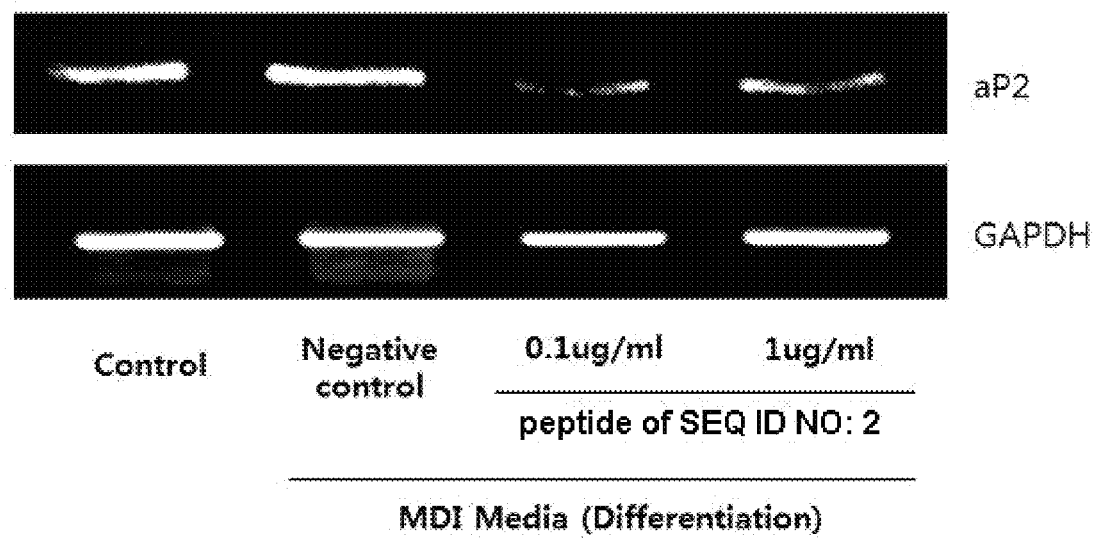
FIG. 3b shows measurement results of the expression levels of the gene aP2, which is involved in adipogenesis, after treatment with the peptide of SEQ ID NO: 3.
Figure 3C:
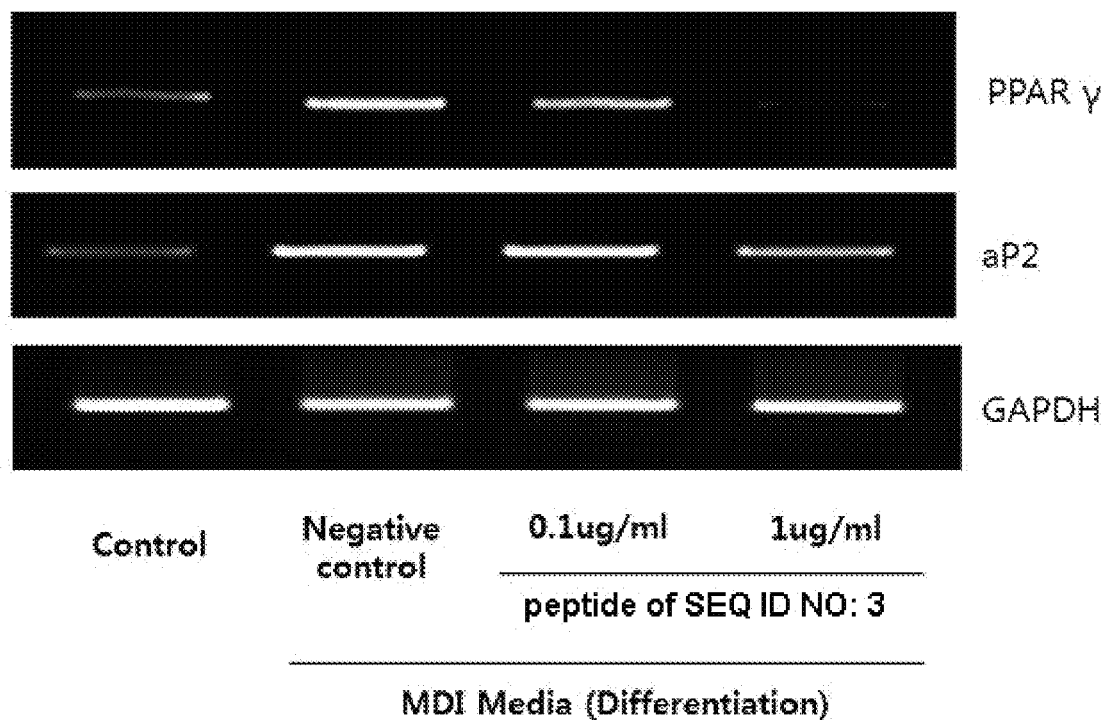
FIG. 3c shows measurement results of the expression levels of the gene aP2, which is involved in adipogenesis, after treatment with the peptide of SEQ ID NO: 5.

In the mouse osteoblast cell line 3T3-L1 which was incubated with the peptide of SEQ ID NO: 1, 3, or 5 for three days, decreased expression levels of the adipogenic marker aP2 were observed (FIGS. 3a-3c).

Figure 4:
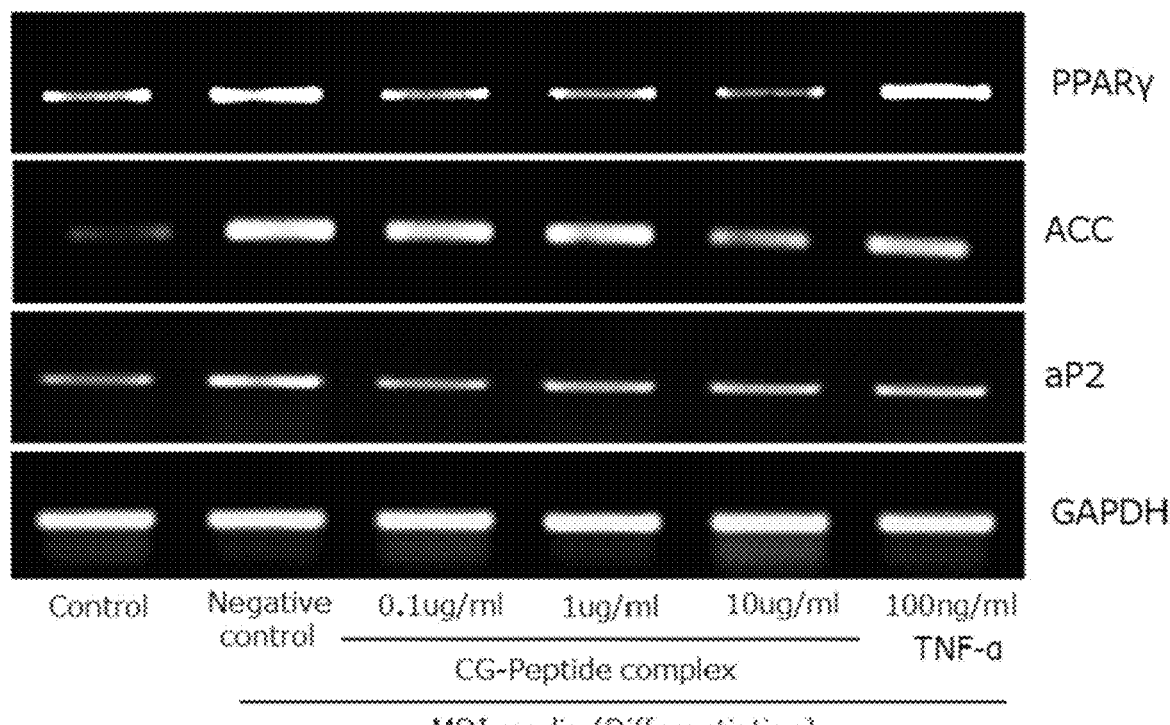
FIG. 4 shows measurement results of expression levels of PPARγ, ACC, and aP2 genes, which play an important role in adiapgenesis, after treatment with various concentrations of the peptide complex of the present invention.

Also, when incubated for three days with concentrations of 0.1 μg/ml, 1 μg/ml, and 10 μg/ml of a complex of peptides of SEQ IS Nos: 1, 3 and 7, the mouse osteoblast cell line was observed to decrease in the expression of the adipogenic markers PPARγ, ACC, and aP2, like the positive control cells treated with 100 ng/ml TNFα (FIG. 4).

1-3. Expression Observation of Adipogenesis and Lipolysis Inducing Proteins by Use of Pre-adipocyte 3T3-L1 cells (pre-adipocytes) were seeded at a density of 3×105 cells/well into 6-well plates. After 24 hours of culturing, the cells were incubated for 14 days with predetermined concentrations (0.1, 1, and 10 μg/ml) of the peptide complex in a 37° C. incubator. Cell lysates obtained by treatment with a cell lysis buffer were used for protein quantitation, followed by Western blotting with an anti-PPARγ antibody (Santa Cruz Biotechnology, USA), which is an antibody against an adipogenic marker, and an anti-pHSL antibody (Santa Cruz Biotechnology, USA), which is an antibody against an lipolytic marker.

Figure 5:
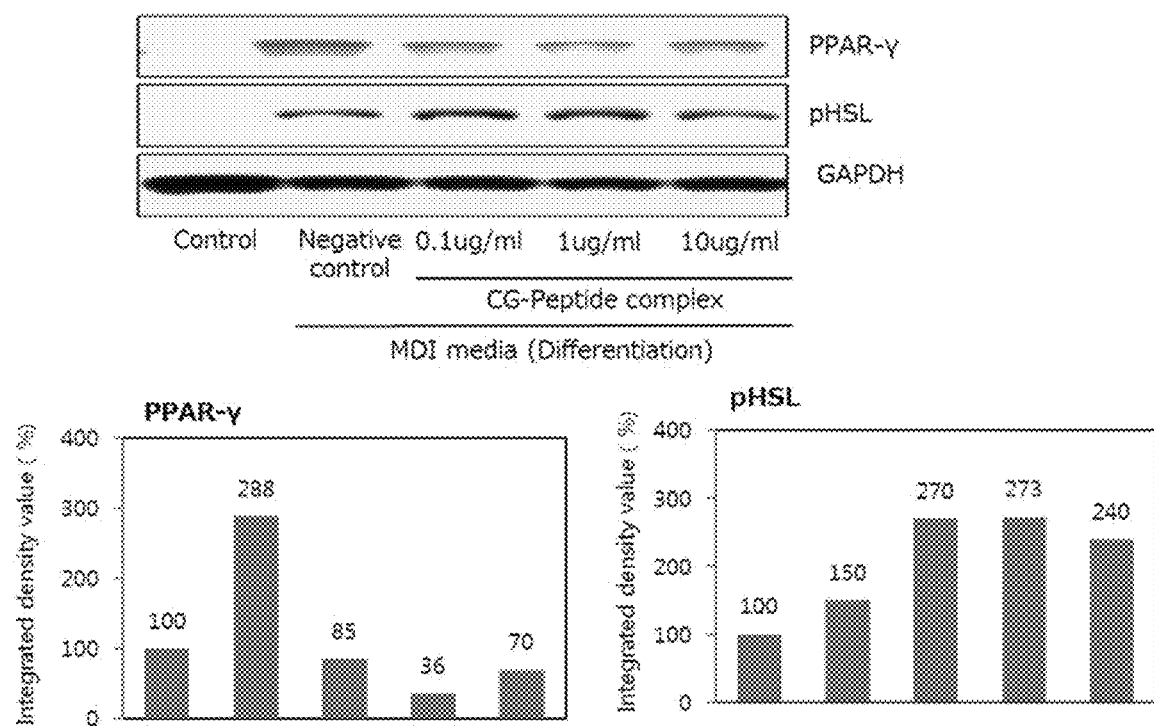
FIG. 5 shows measurement results of expression levels of PPARγ and phospho-HSL, which play an important role in adipogenesis, after various concentrations of the peptide complex of the present invention.

When treated with the peptide complex by concentration, the cells were observed to decrease in the expression of the adipogenic marker PPARγ in a dose-dependent manner while all increasing in the expression of the lipolysis marker pHSL (FIG. 5).

Example 2: Assay for Lipolytic Activity 2-1. Increased Expression of Genes Involved in Lipolysis 3T3-L1 cells (pre-adipocytes) were seeded at a density of 3×105 cells/well into 6-well plates. After 24 hours of culturing, the cells were incubated for 14 days with predetermined concentrations (0.1, 1, and 10 μg/ml) of the peptides in a 37° C. incubator (positive control: 100 ng/ml TNFα (SIGMA)). The cells were harvested and treated with an RNA extraction solution (Easy Blue, Intron) to prepare RNA from which cDNA was then synthesized using an RT premix (Intron). PCR was performed using primers for markers (AMPK-α1 and CGI58), and a PCR premix (Intron).

Target-specific primer sequences for PCR of lipolytic markers were as follows: AMPK-α1 forward primer sequence, 5'-TGACCGGACATAAAGTGGCTGTGA-3' and AMPK-α1 reverse primer, 5'-TGATGATGTGAGGGT-GCCTGAACA-3' (annealing temperature, 60° C.); CGI58 forward primer sequence, 5'-TGTGCAGGACTCTTACT-TGGCAGT-3' and CGI58 reverse primer, 5'-GTTTCTTTGGGCAGACCGGTTTCT-3' (annealing temperature, 60° C.)

PCR products were each loaded in a volume of 5 μl into a 1% agarose gel, and electrophoresed, followed by identifying bands in a Gel-Doc.

Figure 6A:
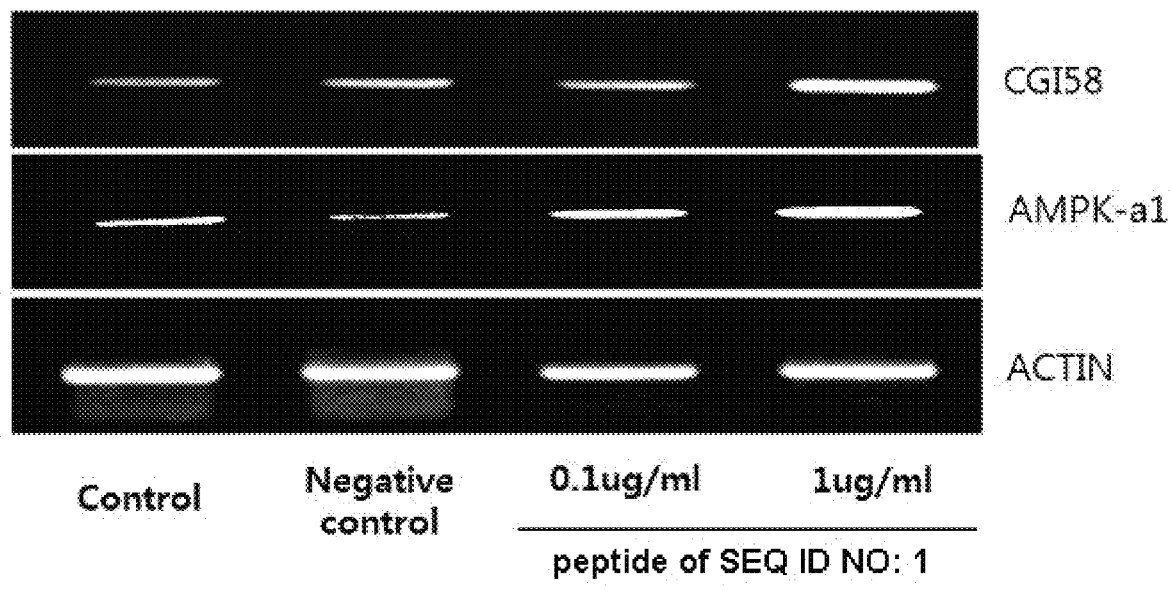
FIG. 6a shows measurement results of expression levels of AMPK-α1 and CGI58 genes, which are involved in the degradation of accumulated fats, after treatment with the peptide of SEQ ID NO: 1.
Figure 6B:
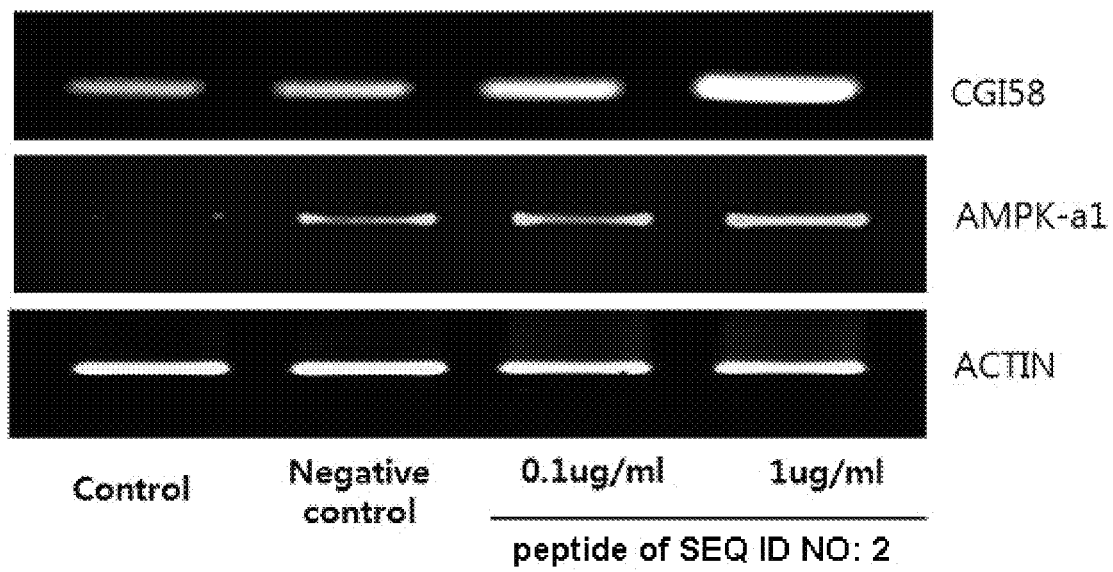
FIG. 6b shows measurement results of expression levels of AMPK-α1 and CGI58 genes, which are involved in the degradation of accumulated fats, after treatment with the peptide of SEQ ID NO: 3.
Figure 6C:
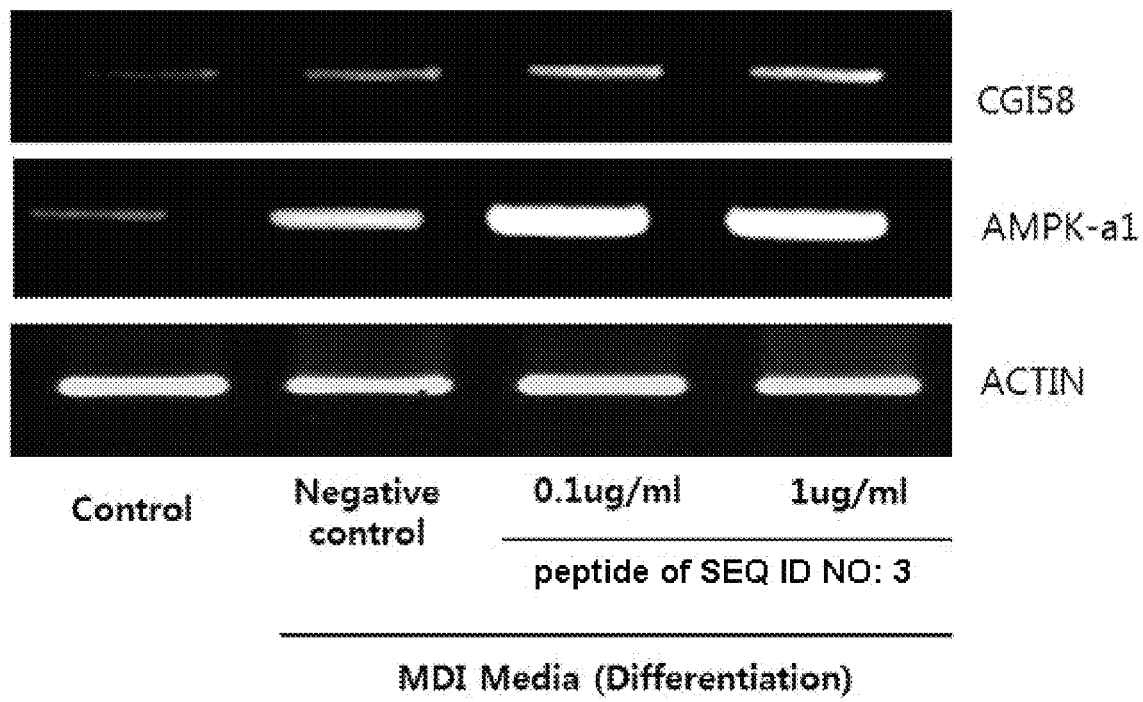
FIG. 6c shows measurement results of expression levels of AMPK-α1 and CGI58 genes, which are involved in the degradation of accumulated fats, after treatment with the peptide of SEQ ID NO: 5.
Figure 6D:
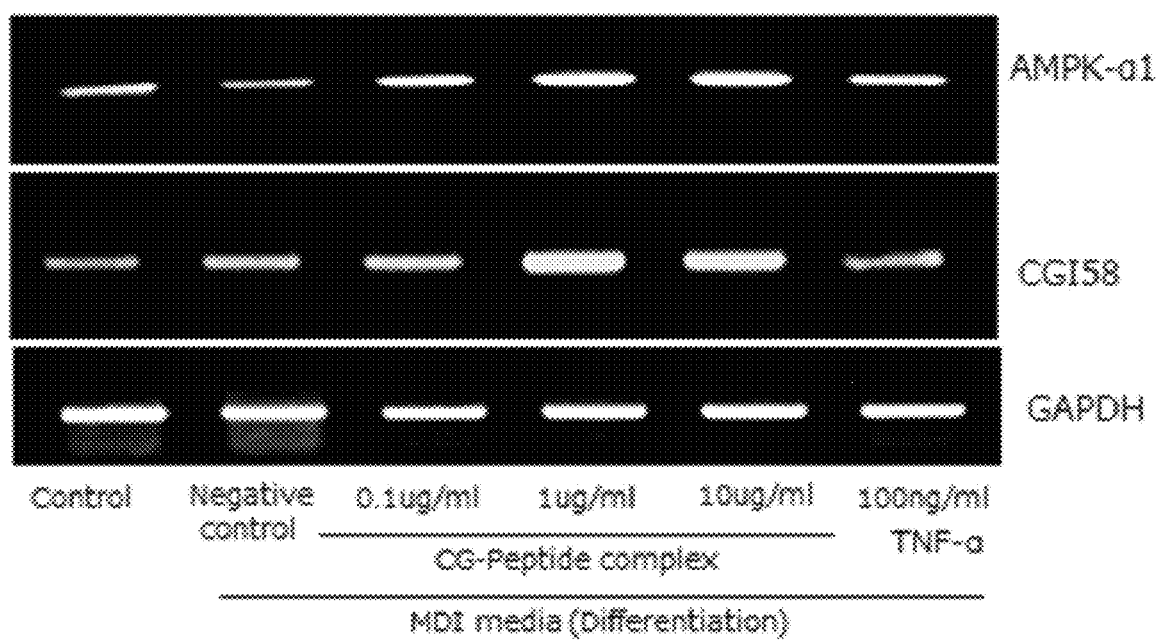
FIG. 6d shows measurement results of expression levels of AMPK-α1 and CGI58 genes, which are involved in the degradation of accumulated fats, after treatment with a complex of peptides of SEQ ID NOS: 1, 3, and 7.

In all of the pre-adipocytes (3T3-L1) which were incubated with the peptides, increased expression levels of the lipolytic markers AMPK-α1 and CGI-58 were detected (FIGS. 6a-6c). In addition, treatment with the peptide complex was observed to increase the expression of AMPK-α1 and CGI-58 in dose-dependent manners and to higher levels compared to the positive control TNFα 100 ng/ml treatment (FIG. 6d).

2-2. Expression Observation of Lipolysis Inducing Proteins by Use of Pre-adipocyte 3T3-L1 cells (pre-adipocytes) were seeded at a density of 3×105 cells/well into 6-well plates. After 24 hours of culturing, the cells were incubated for 14 days with predetermined concentrations (0.1, 1, and 10 μg/ml) of the peptide complex in a 37° C. incubator (positive control: 100 ng/ml TNFα(SIGMA)). Cell lysates obtained by treatment with a cell lysis buffer were used for protein quantitation, followed by Western blotting with an anti-ATGL antibody (Santa Cruz Biotechnology, USA), which is an antibody against an lipolytic marker.

Figure 7:
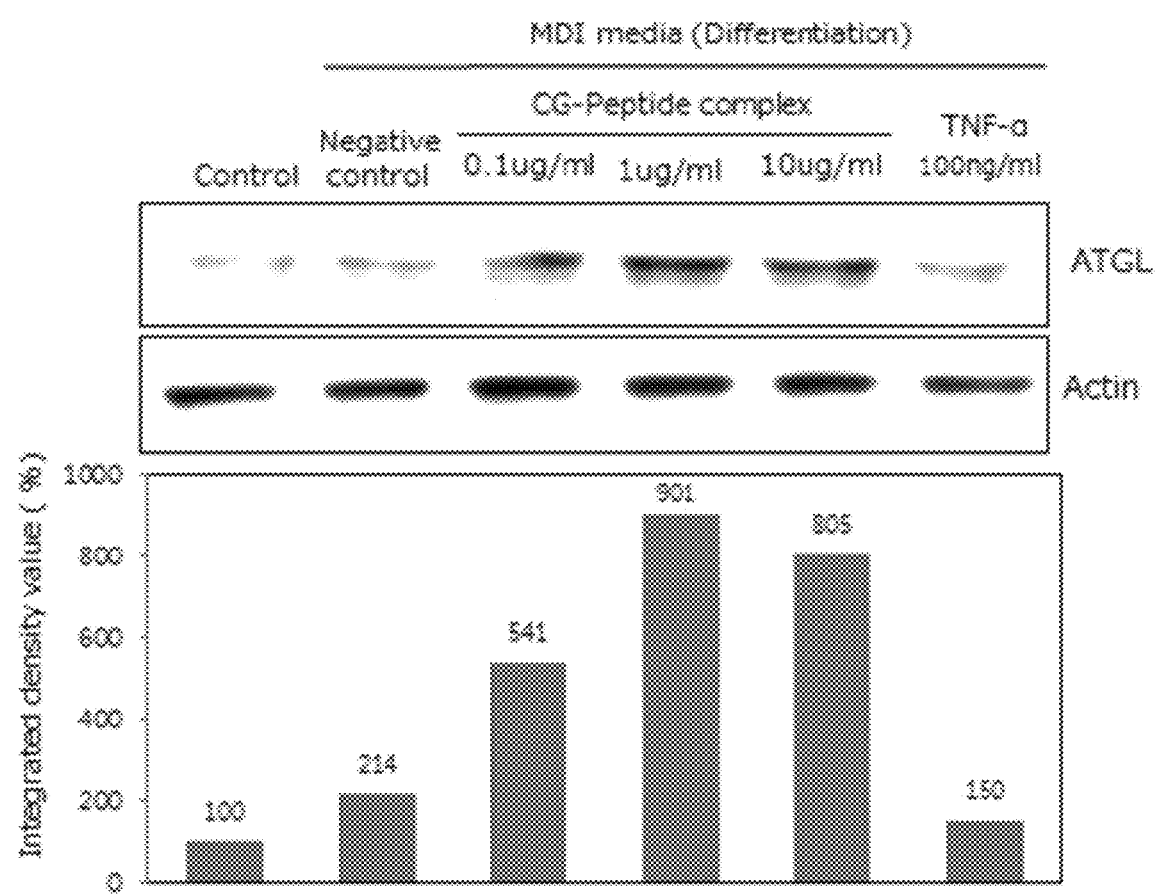
FIG. 7 shows measurement results of ATGL, a protein involved in the degradation of accumulated fats, after treatment with various concentrations of the peptide complex of the present invention.

The expression of the lipolytic marker ATGL was increased by treatment with the peptide complex (FIG. 7).

2-3. Fluorescence Microscopic Observation of Expression of Lipolysis Inducing Protein by Use of Pre-adipocyte 3T3-L1 cells (pre-adipocytes) were seeded at a density of 3×105 cells/well into 6-well plates. After 24 hours of culturing, the cells were incubated for 14 days with the individual peptides or the peptide complex (1 μg/ml) in a 37° C. incubator (positive control: 100 ng/ml TNFα (SIGMA)). Thereafter, the cells were fixed with 70% ethanol and then subjected to immunostaining with an anti-phospho-HSL antibody (Santa Cruz Biotechnology, USA) to observe the cellular expression of phospho-HSL, a lipolytic marker.

Figure 8A:
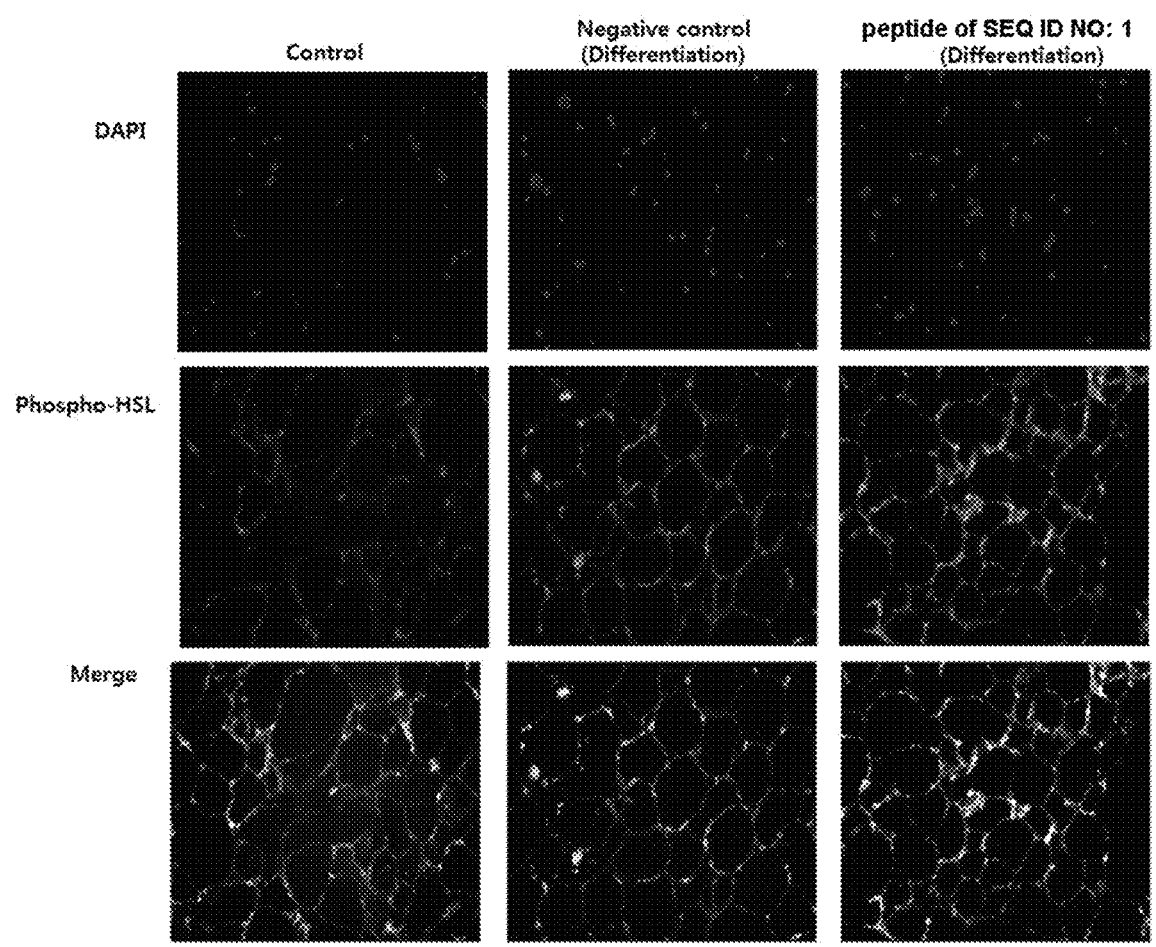
FIG. 8a shows results of expression levels of the Phospho-HSL protein involved in the degradation of accumulated fats, after treatment with the peptide of SEQ ID NO: 1.
Figure 8B:
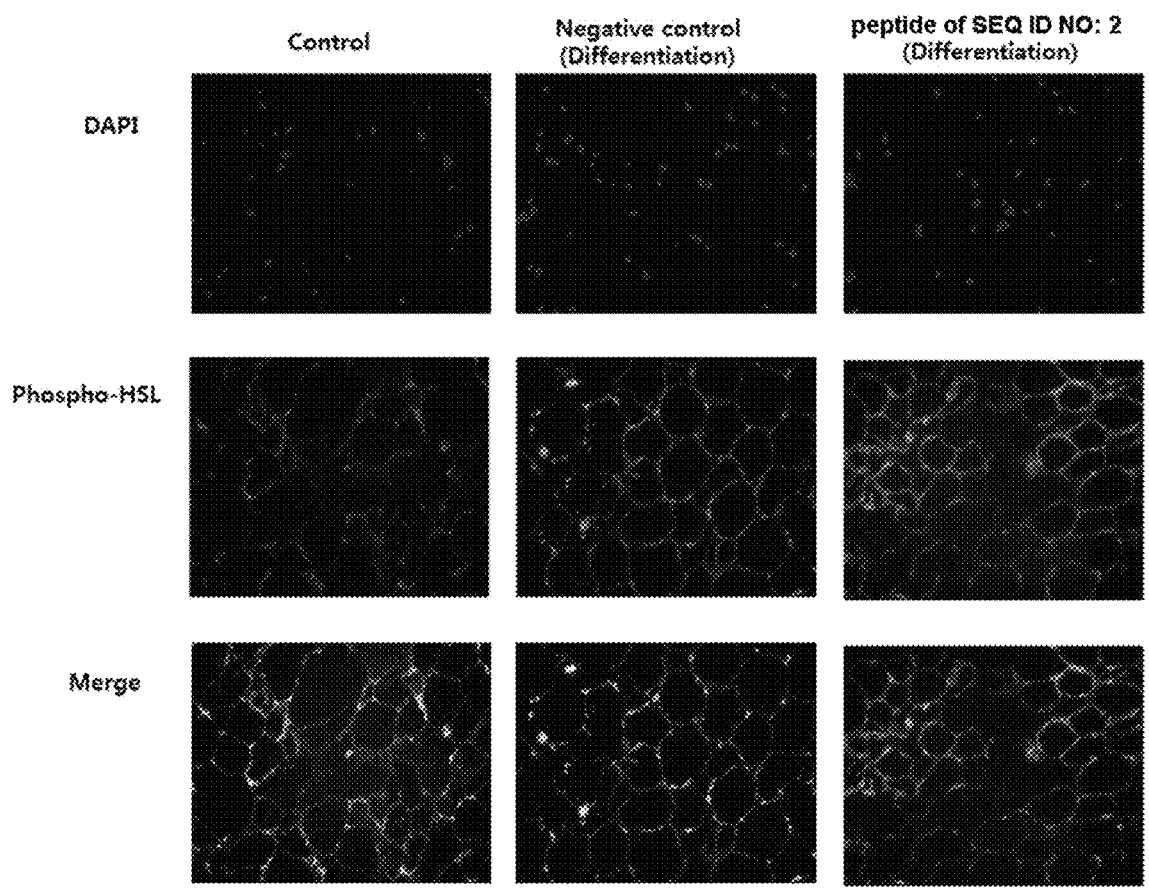
FIG. 8b shows results of expression levels of the Phospho-HSL protein involved in the degradation of accumulated fats, after treatment with the peptide of SEQ ID NO: 3.
Figure 8C:
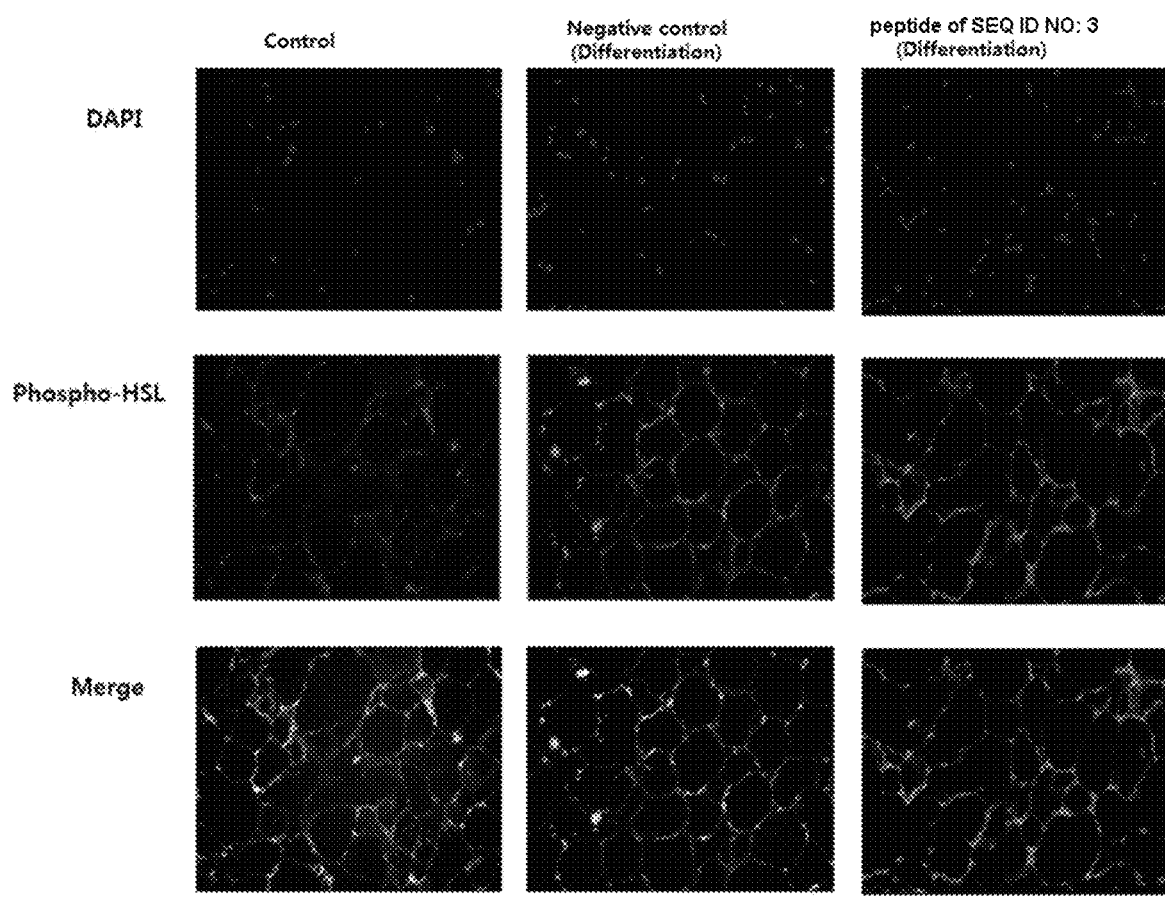
FIG. 8c shows results of expression levels of the Phospho-HSL protein involved in the degradation of accumulated fats, after treatment with the peptide of SEQ ID NO: 5.
Figure 8D:
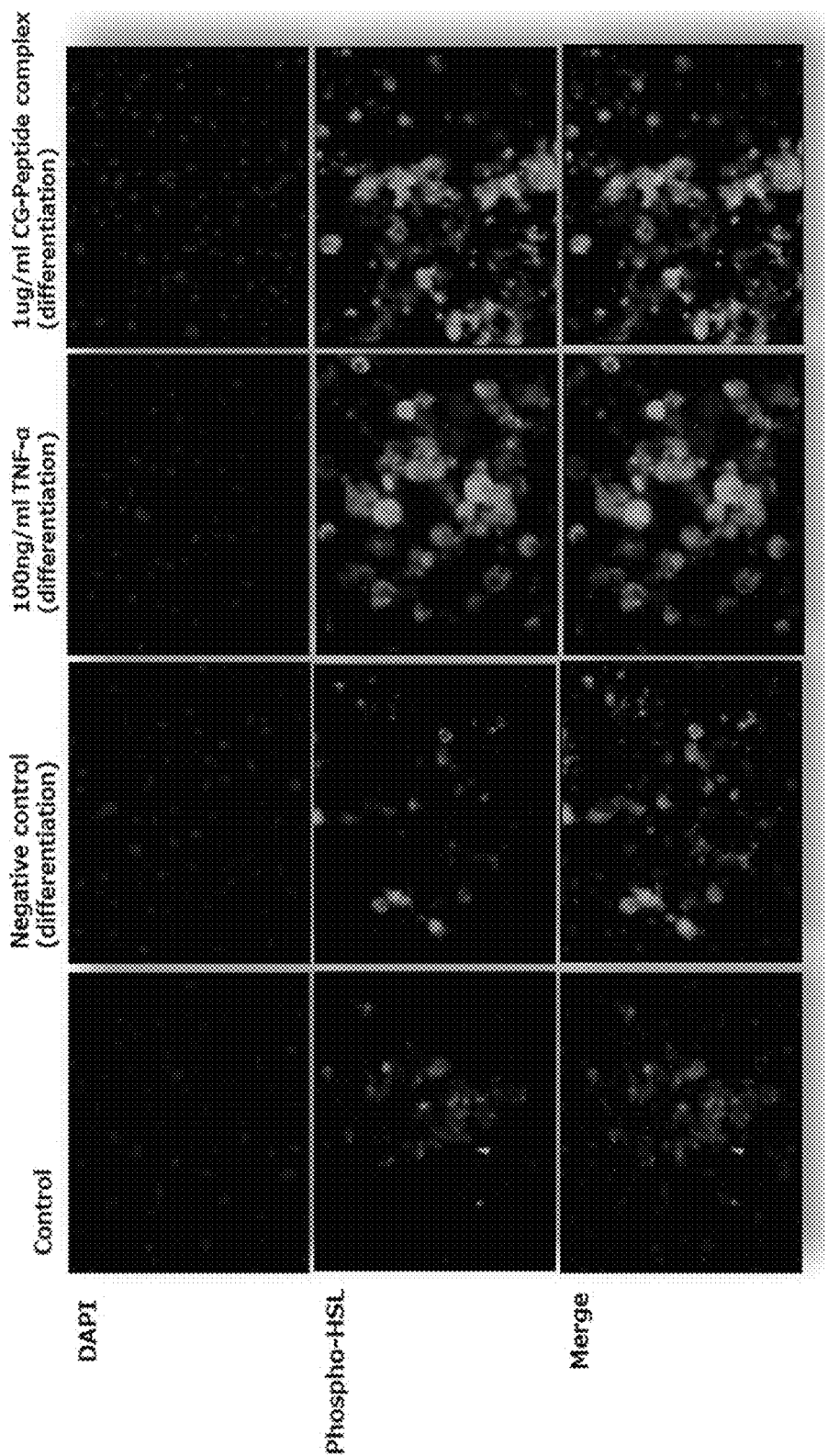
FIG. 8d shows results of expression levels of the Phospho-HSL protein involved in the degradation of accumulated fats, after treatment with a complex of peptides of SEQ ID NOS: 1, 3, and 7, as measured by immunostaining.

From the experimental data, the peptides alone (FIGS. 8a-8c) and the peptide complex (FIG. 8d) were both observed to increase the expression of the lipolytic marker phospho-HSL.

2-4. Quantitation of Lipolysis Product Glycerol

After being taken from the abdomens of obesity-induced mice, adipose tissues were plated at a density of 100 mg/well into 24-well culture plates and cultured in a culture medium (1 ml Krebs-Ringer buffer containing 25 mM HEPES, 5.5 mM glucose, and 2% (w/v) bovine serum albumin). In this regard, the tissues were incubated for 48 hours with 0.1 μg/ml, 1 μg/ml, and 10 μg/ml of the peptide complex whereas 100 ng/ml of TNFα was used as a positive control. Glycerol produced during lipolysis was quantitatively analyzed.

Figure 9:
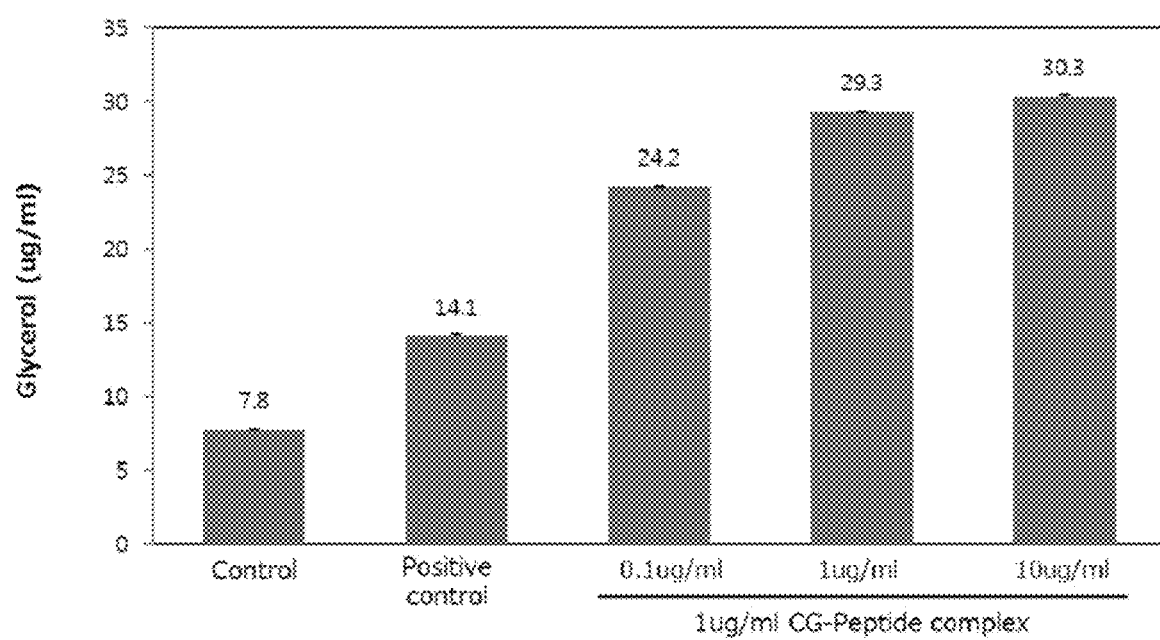
FIG. 9 shows measurement results of glycerol produced after treatment with various concentrations of the peptides complex of the present invention.

As is understood from the experimental data, the amount of glycerol resulting from lipolysis by treatment with the peptide complex was increased in a dose-dependent manner and greater than that produced upon treatment with the positive control TNFα (FIG. 9). 2-5. Lysis effect on adipose tissue isolated from obese mouse Adipose tissues are divided into white fat and brown fat by color and into subcutaneous fat, abdominal fat, mesentery fat (visceral fat), and epididymal fat by tissue. After body anatomization, lipoectomy was performed on the tissues. White fats were isolated, plated in an amount of 100 mg/well into 24-well plates, and then incubated for 72 hours with concentrations of the peptide complex in a culture medium (1 ml Krebs-Ringer buffer containing 25 mM HEPES, 5.5 mM glucose, and 2% (w/v) bovine serum albumin). The fats were sectioned into slices which were than dyed with hematoxylin and eosin. Sizes of adipocytes were compared under a microscope (TS100 Nikon) with 100× magnification.

Figure 10A:
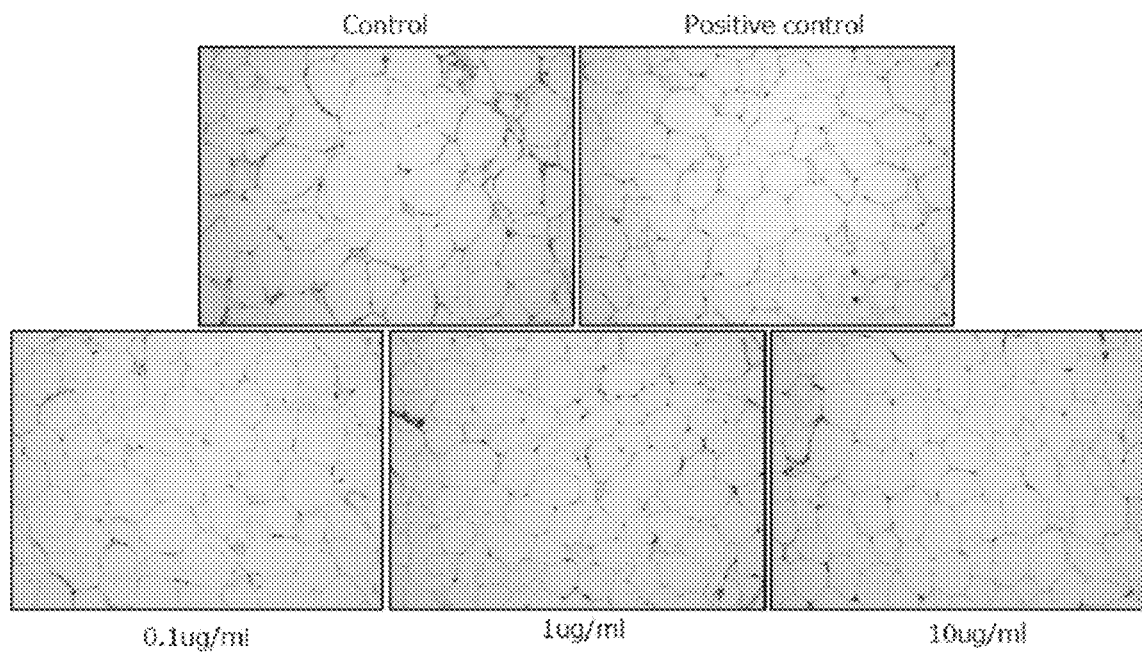
FIG. 10a shows adipose tissues degraded in obese mouse experiment models after treatment with the peptide complex of the present invention.
Figure 10B:
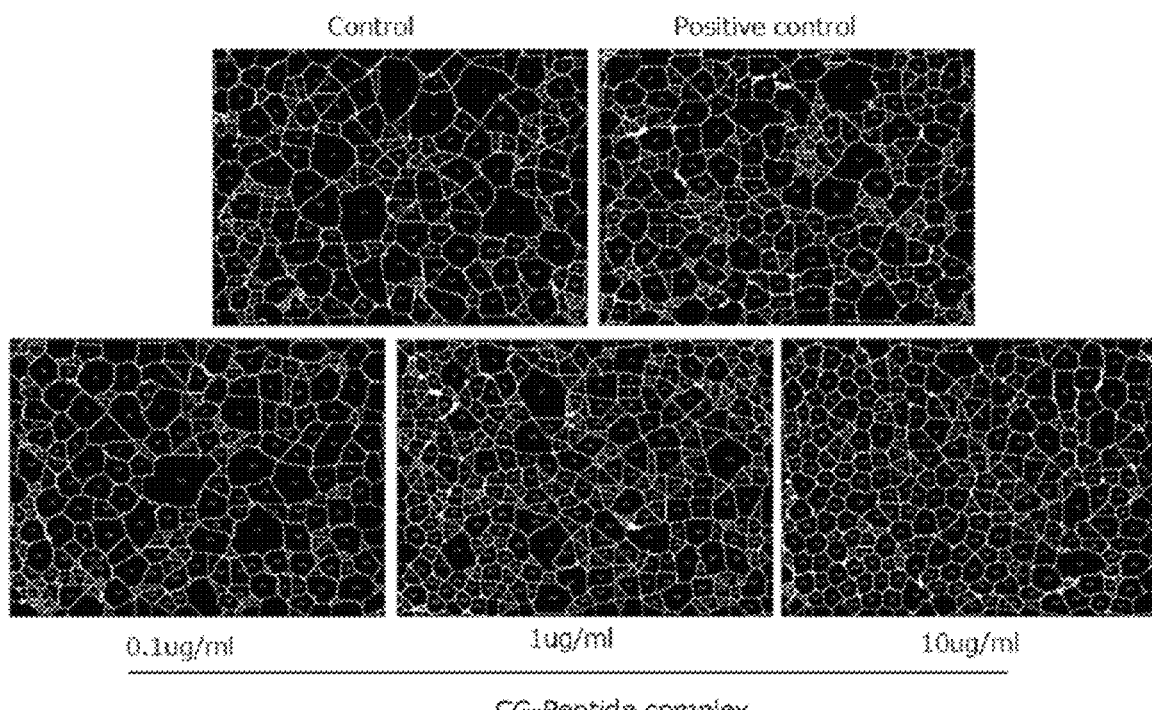
FIG. 10b shows sizes and numbers of the adipose tissues degraded in obese mouse experiment models after treatment with the peptide complex of the present invention.

Compared to the control, the fats treated with various concentrations of the peptides decreased in size (FIG. 10a). In addition, when treated with the peptide complex, adipose tissues having distinct cell membrane compartments were observed in cell size, as measured by a program (FIG. 10b).

2-6. Observation of Lipolytic Marker in Adipose Tissue

An adipose tissue taken from the abdomen of an obesity-induced mouse was plated in an amount of 100 mg per well into 24-well culture plates and incubated for 48 hours with the peptide complex while TNFα 100 ng/ml was used as a positive control. The labeled lipolytic marker phospho-HSL (green fluorescent) was detected.

Figure 11:
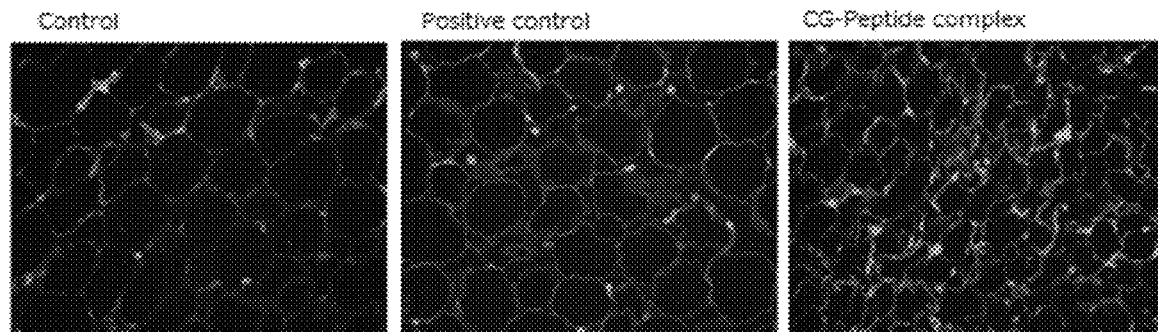
FIG. 11 shows results of the expression levels of the Phospho-HSL protein which is involved in the degradation of accumulated fats after treatment with the peptide complex of the present invention, as measured by immunostaining.

Treatment with the peptide complex was observed to increase the expression level of the lipolytic marker phospho-HSL in adipose tissues (FIG. 11).

Example 3: Adipogenesis-Suppressive and Lipolysis-Promotive Effect in Experimental Animal Weight Loss and Adipogenesis Suppression in High-fat Diet-fed Animal Models DIO (diets induced obesity), which had become obese by feeding high-fat diets thereto, were used for anti-obesity experiments in which TNFα 5 µg/ml was used as a positive control. For a control, a general diet, not a high-fat diet, was fed. In the experiment, a high-fat diet was fed for 12 weeks while the peptide complex or the positive control was applied. During the experiment, the weight was monitored.

TNFα and the anti-obesity compounds were intraperitoneally injected at PM 3-4 o'clock every week for 12 weeks. Weights and meal sizes were measured just before the initial injection and then regularly at intervals of one week. Blood samples were taken from tail veins after the experiments of drug injection and measured for blood sugar levels, using Accu-Check Active (Roche) and analyzed for cholesterol levels, using Cholesterol calculation Kit (BioVision). Adipose tissues are divided into white fat and brown fat by color and into subcutaneous fat, abdominal fat, mesentery fat (visceral fat), and epididymal fat by tissue. After lipoectomy, the fats thus obtained from the tissues were observed. For histological examination, the fats were fixed with 10% neutral buffered formalin, embedded in paraffin blocks, cut into 5 µm-thick sections, and dyed with hematoxylin and eosin. To analyze the phosphorylation of the lipolytic marker HSL, fluorescent staining was carried out with an anti-pHSL antibody. A tissue sample was made, mounted on glycerine jell mounting media, and covered with a cover glass. The tissues were observed under a microscope (Nikon, TS100), with a built-in digital camera taking images thereof.

Figure 12:
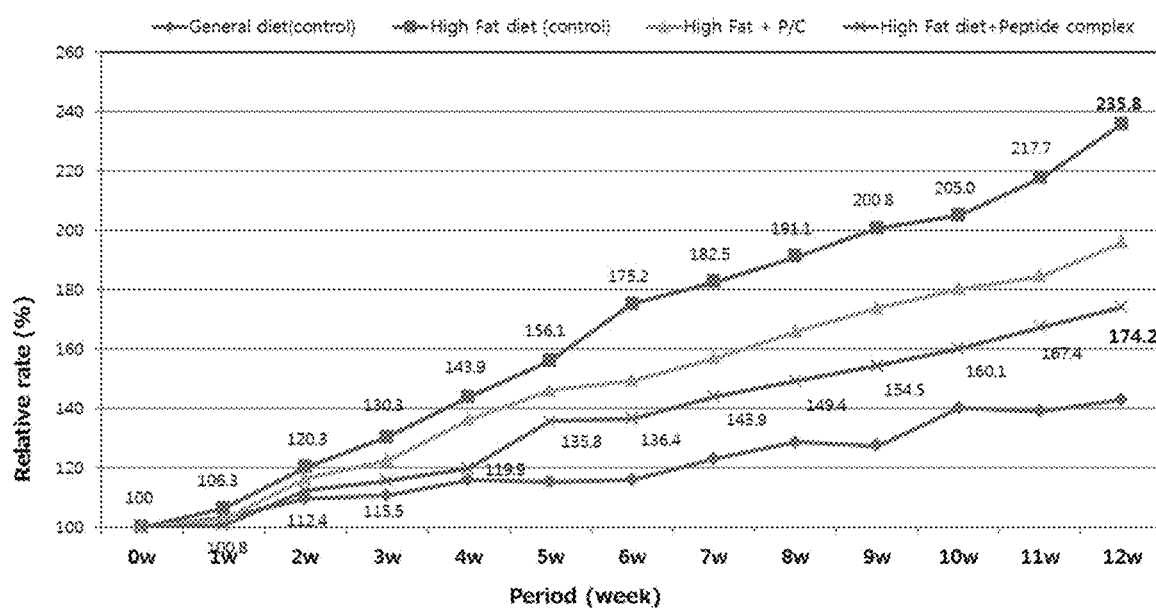
FIG. 12 shows changes in body weight (g) and diet intake of obese mice after treatment with the peptide complex of the present invention.

Over 12 weeks from the initial stage to the final stage of the experiment, mice were measured to increase in weight from 20.9 g to 28.74 g when fed with a general diet and from 20.99 g to 49.5 g when fed with a high-fat diet. In the mice fed with a high-fat diet with the peptide complex injected thereto, the weight gain was reached only to 36.76 g after 12 weeks from the initial weight of 21.1 g, indicating a significant reduction of weight gain (174.2%), compared to the high-fat diet-fed control (235.8%) (Table 2 and FIG. 12).

TABLE 2

Weight of Obese Mouse Model after Treatment with Peptide Complex

|  | General Diet (control) | High fat diet (control) | H.F + P/C | H.F + P. Complex |
|---|---|---|---|---|
| Weight (g) | | | | |
| 0 w | 20.09 | 20.99 | 22.41 | 21.1 |
| 1 w | 20.75 | 22.32 | 23 | 21.26 |
| 2 w | 21.99 | 25.25 | 26.12 | 23.72 |
| 3 w | 18.23 | 27.35 | 27.45 | 24.36 |
| 4 w | 23.26 | 30.2 | 30.51 | 25.29 |
| 5 w | 23.16 | 32.76 | 32.76 | 28.65 |
| 6 w | 23.28 | 36.78 | 33.49 | 28.79 |
| 7 w | 24.71 | 38.31 | 35.14 | 30.37 |
| 8 w | 25.84 | 40.12 | 37.15 | 31.53 |
| 9 w | 25.59 | 42.14 | 38.97 | 32.59 |
| 10 w | 28.13 | 43.02 | 40.39 | 33.78 |
| 11 w | 27.9 | 45.7 | 41.35 | 35.33 |
| 12 w | 28.74 | 49.5 | 43.91 | 36.76 |
| Weight (%) | | | | |
| 0 w | 100 | 100 | 100 | 100 |
| 1 w | 103.3 | 106.3 | 102.6 | 100.8 |
| 2 w | 109.5 | 120.3 | 116.6 | 112.4 |
| 3 w | 90.7 | 130.3 | 122.5 | 115.5 |
| 4 w | 115.8 | 143.9 | 136.1 | 119.9 |
| 5 w | 115.3 | 156.1 | 146.2 | 135.8 |
| 6 w | 115.9 | 175.2 | 149.4 | 136.4 |
| 7 w | 123.0 | 182.5 | 156.8 | 143.9 |
| 8 w | 128.6 | 191.1 | 165.8 | 149.4 |
| 9 w | 127.4 | 200.8 | 173.9 | 154.5 |
| 10 w | 140.0 | 205.0 | 180.2 | 160.1 |
| 11 w | 138.9 | 217.7 | 184.5 | 167.4 |
| 12 w | 143.1 | 235.8 | 195.9 | 174.2 |

Figure 13:
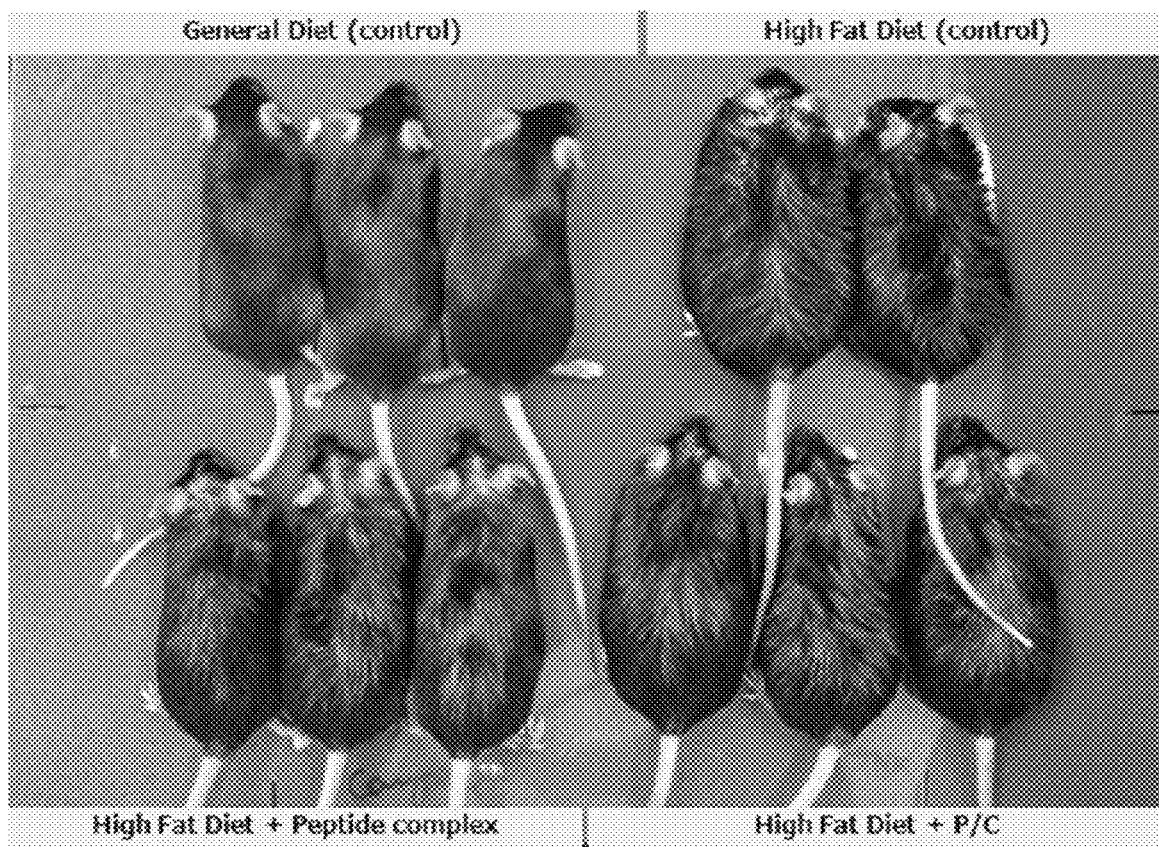
FIG. 13 shows images of obese mice after treatment of the peptide complex of the present invention.

After completion of the 12-week experiment, in addition, the mice treated with the peptide complex, were observed to maintain their body sizes in similar patterns to those of the normal mice (general diet), but not to those of the high-fat diet-fed mice, as analyzed on the images (FIG. 13).

Figure 14:
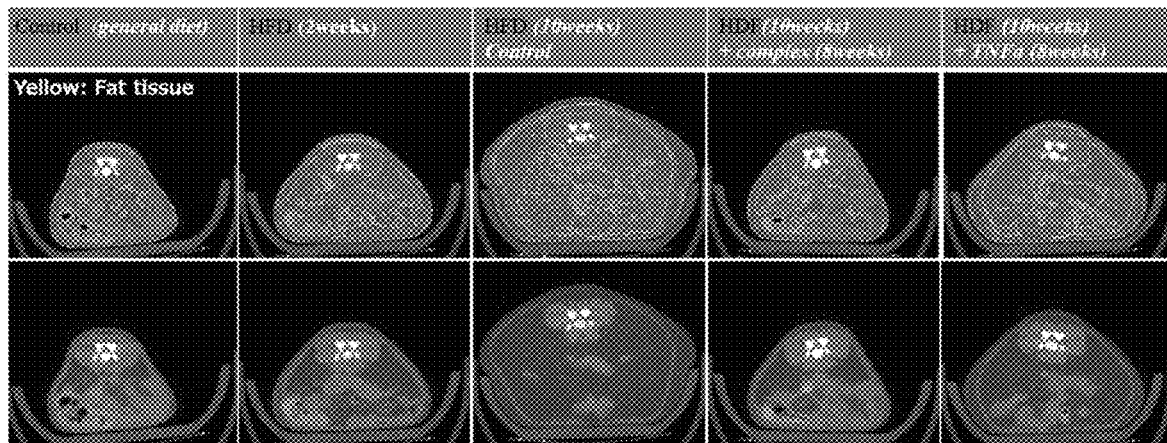
FIG. 14 shows results of fat distribution in obese mouse models induced by feeding a high-fat diet to the experimental animal model C57BL/6, as analyzed by micro-CT.

After 12 weeks of the experiment, the mice were subjected to micro-CT to examine fat distribution across the body. As a result of the micro-CT data of fats (yellow) in the body, the fat distributed across the body was remarkably increased in the high-fat diet-fed mice, compared to the general diet-fed control while a significantly reduced level of fats distributed across the body was observed in the group which were treated with the peptide complex with the high-fat diet fed thereto (FIG. 14).

Figure 15:
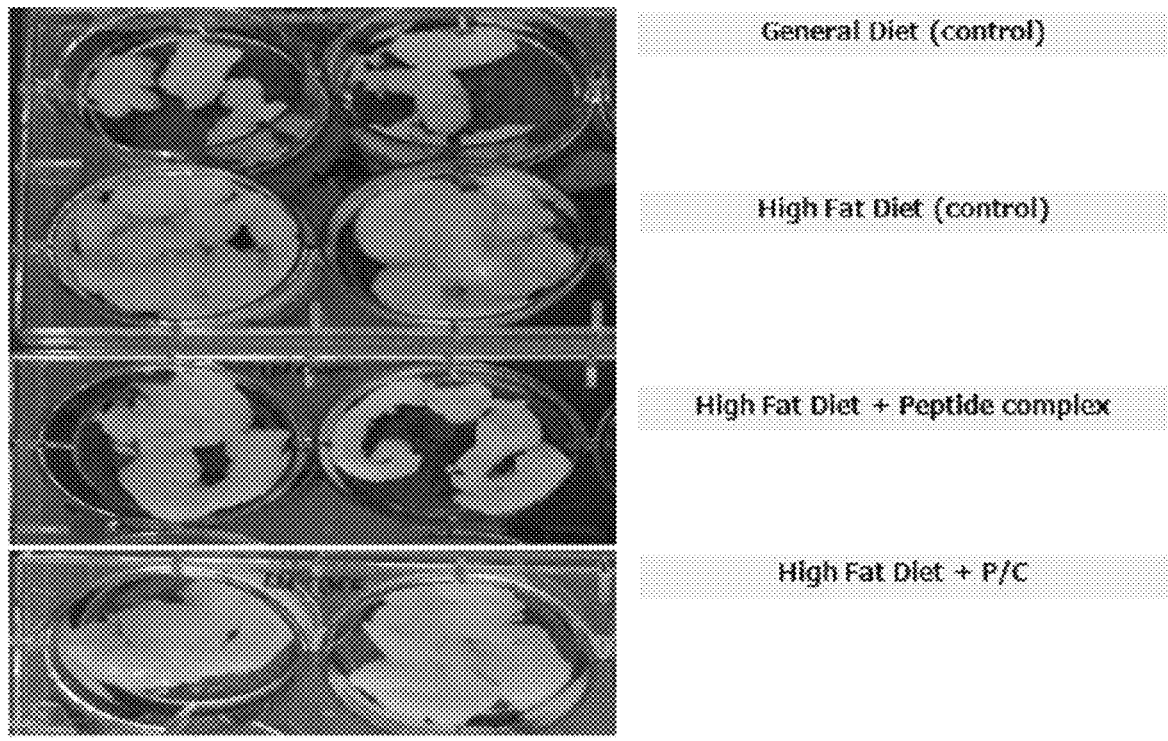
FIG. 15 shows images of the adipocyte tissues extracted from obese mouse models induced by feeding a high-fat diet to the experimental animal model C57BL/6, after treatment with the peptide complex of the present invention.

The mice which completed micro-CT imaging were anatomized to extract the adipose tissues distributed across the body. Volumes of the adipose tissues were compared. As a result, the fat extracted from the high-fat diet-fed mice was greater than that from the general diet-fed mice, with a significant reduction in the fat volume in the mice treated with the peptide complex plus the high-fat diet (FIG. 15).

Figure 16A:
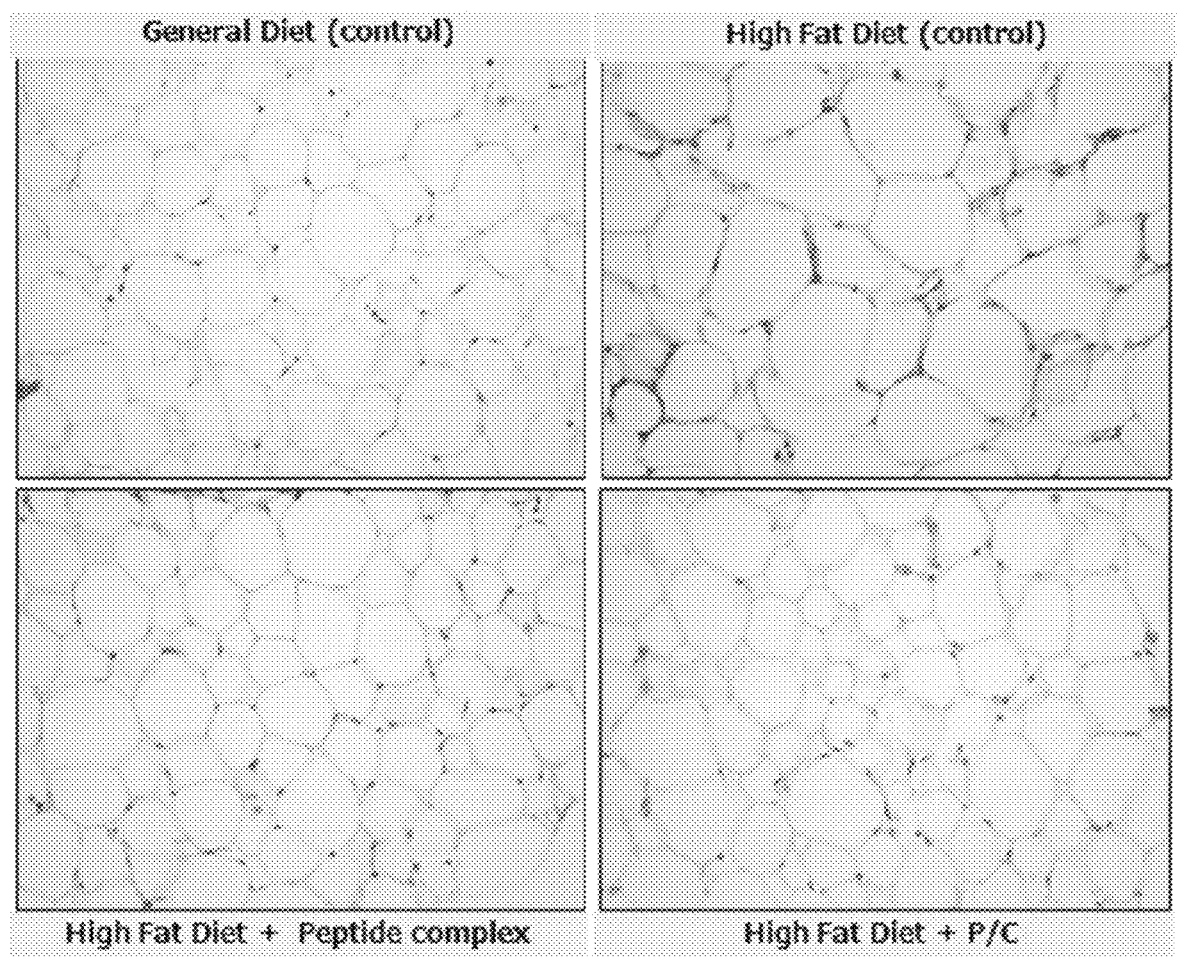
FIG. 16a shows morphological images of the adipocytes in adipose tissues taken from obese mouse models induced by feeding a high-fat diet to the experimental animal model C57BL/6, after treatment with the peptide complex of the present invention.
Figure 16B:
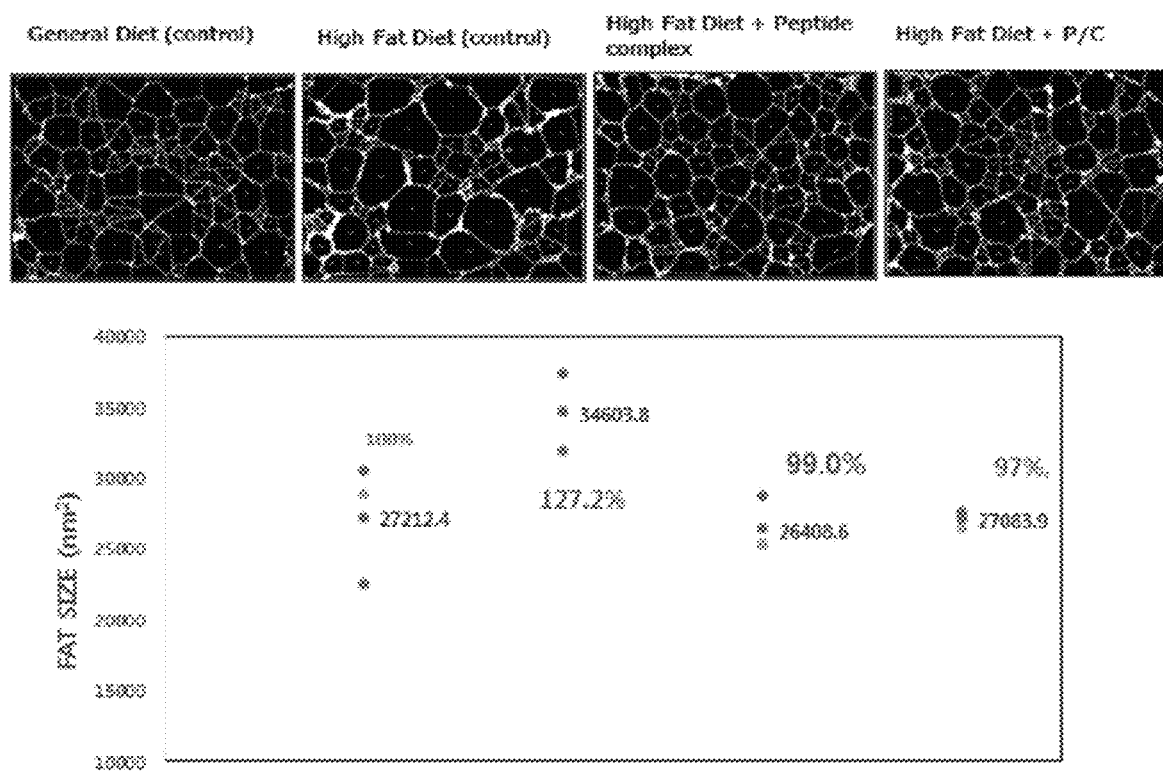
FIG. 16b shows size results of the adipocytes in the adipose tissues taken from obese mouse models induced by feeding a high-fat diet to the experimental animal model C57BL/6, after treatment with the peptide complex of the present invention.

Fats were isolated, and dyed with H&E to visualize fat sizes. Smaller sizes of fats were observed in the mice treated with both the high-fat diet and the peptide complex than in the high-fat diet-fed control (FIG. 16a). Fat size analysis through a program showed that, when the fat size of the general diet-fed control was assumed to be 100%, a fat size was increased to 127% in the high-fat diet-fed group, but decreased to 97% in the group treated with the high-fat diet and the peptide complex (FIG. 16b).

Figure 17:
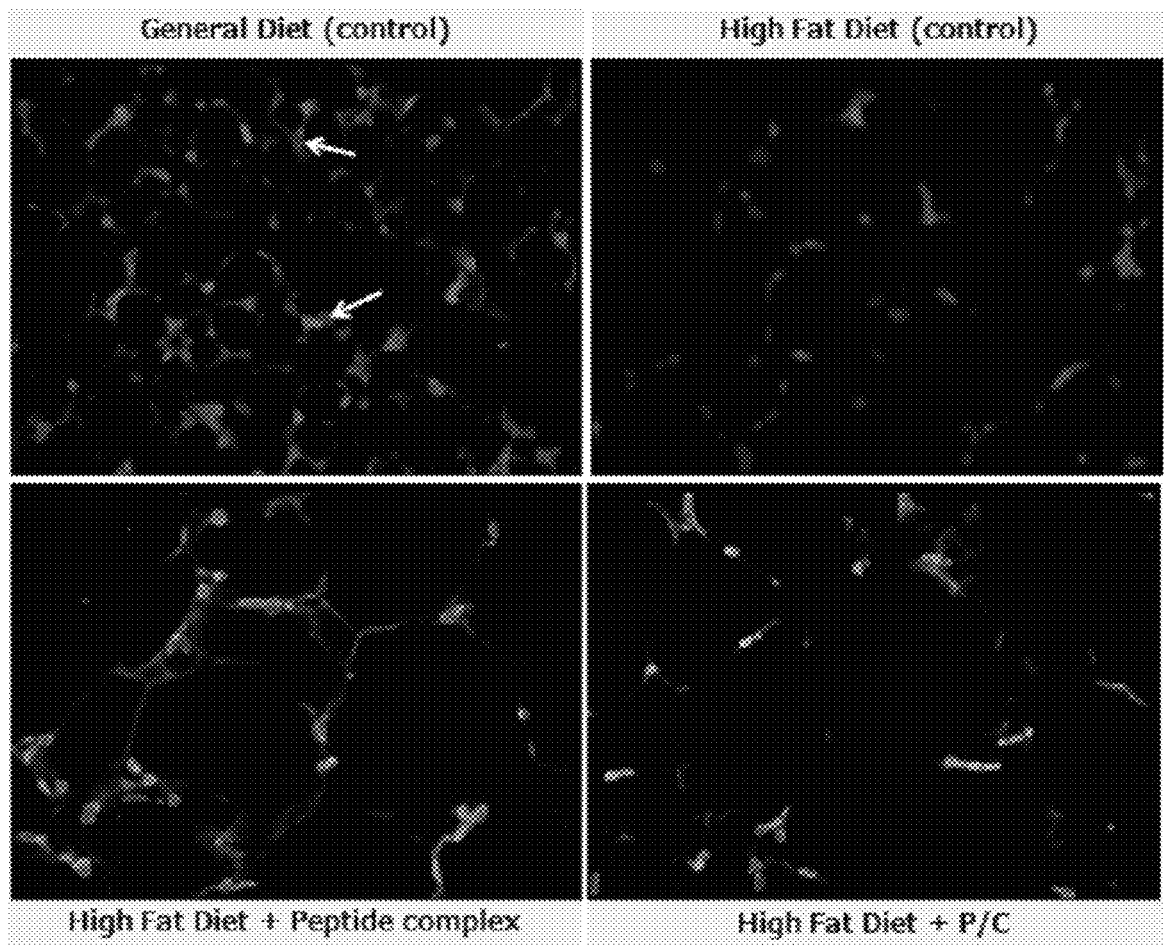
FIG. 17 shows measurement results of the expression levels of the phosphor-HSL protein, which is involved in lipolysis, in adipocytes of adipose tissues taken from obese mouse models induced by feeding a high-fat diet to the experimental animal model C57BL/6, after treatment with the peptide complex of the present invention.

The fats were isolated and examined for the expression level of the lipolytic marker phospho-HSL in adipose tissues. The mice treated with both the high-fat diet and the peptide complex were observed to have an elevated expression level of phospho-HSL (FIG. 17).

Figure 18:
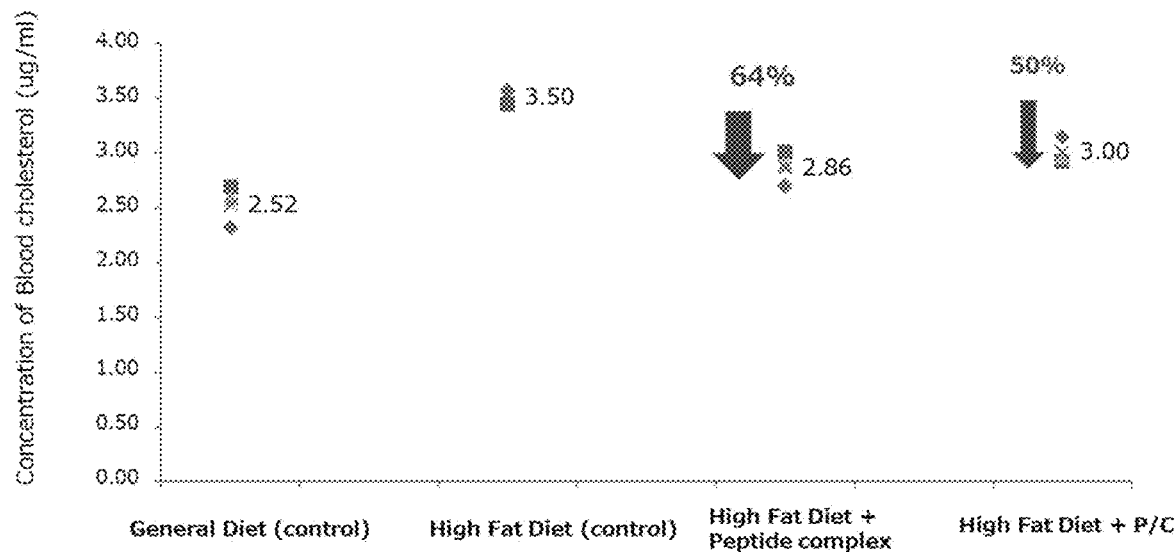
FIG. 18 shows measurement results of cholesterol levels in blood samples taken from obese mouse models induced by feeding a high-fat diet to the experimental animal model C57BL/6, after treatment with the peptide complex of the present invention.

Blood cholesterol levels in the mice after the experiment were measured. As a result, the blood cholesterol level was 2.52 µg/ml in the general diet-fed mice, 3.5 µg/ml in the high-fat diet-fed mice, and 2.86 µg/ml in the mice treated with both the high-fat diet and the peptide complex, indicating that the peptide complex reduced the cholesterol level that elevated with obesity (FIG. 18).

Figure 19:
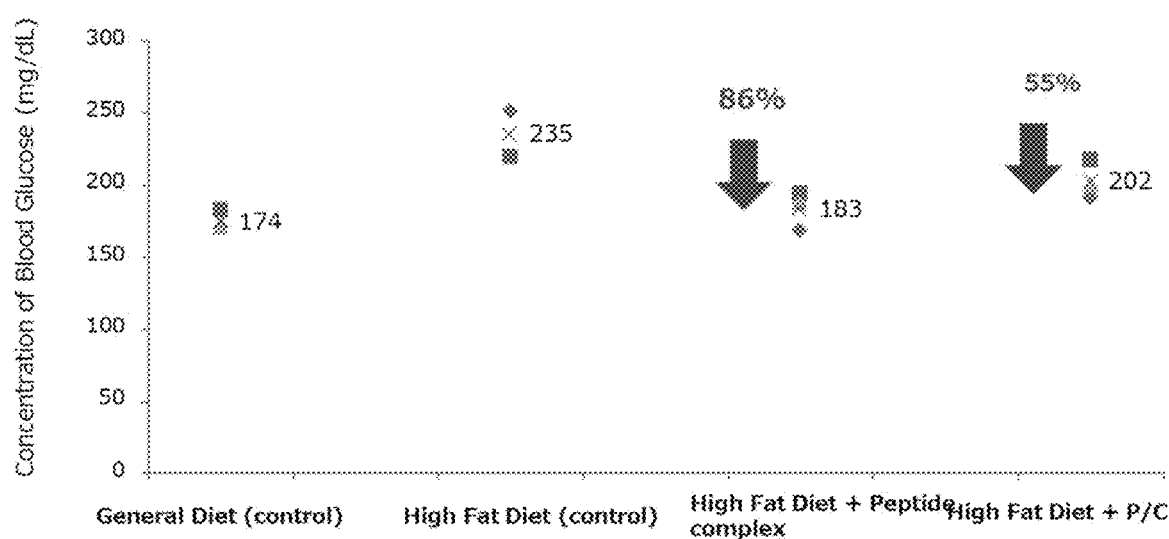
FIG. 19 shows measurement results of glucose levels in blood samples taken from obese mouse models induced by feeding a high-fat diet to the experimental animal model C57BL/6, after treatment with the peptide complex of the present invention.

Blood sugar levels after completion of the experiment were 174 mg/dL in the general diet-fed mice, and increased to 235 mg/dL in the high-fat diet-fed mice. However, a blood sugar level of 183 mg/dL was measured in the mice treated with both the high-fat diet and the peptide complex, with a significant reduction therein (FIG. 19).

Example 4: Blood Sugar Control

Effect on Blood Sugar Control

In this animal experiment, C57BL/6 (normal mouse) (purchased from Samtako Inc.) and female C57BLKS/JLepr (diabetes model mouse, db/db mouse) (purchased from Central Lab. Animal Inc.) were used, together with the peptide complex as an anti-diabetes and/or anti-obesity effective material, and sitagliptin as a positive control drug. In this Example, the anti-diabetes and/or anti-obesity effective complex was evaluated for acute anti-diabetes efficacy (single administration) in a normal mouse model and a genetically potential-diabetic model, using GTT (glucose tolerance test), which is a representative diagnostic method for diabetes. Mice were bred per cage at a temperature of 22-24° C. and a relative humidity of 50-30%, with four per cage. The mice was under 150-300 Lux light from AM 8 o'clock to PM 8 o'clock with 12 light/12 dark cycles. They were given free access to a general diet (18% protein, manufactured in 2018, Harlan Laboratories Inc, USA). To begin with, the mice were starved for 4 hours or longer before ITT experiment and for 12 hours before GTT experiment. The complex was orally administered by force with the aid of a disposable oral administration syringe one hour before GTT experiment. For GTT experiment, the mice were allowed to freely access to a high-fat diet on 0 (zero) hour after experiment started. After 40 min of free access to a high-fat diet, blood samples for use in examining blood glucose levels were taken from the tail vein at intervals of 0, 30, 60, 90, 120, and 180 min. Blood glucose levels were measured using Accu-Chek active (Roche). Sitagliptin, used as a therapeutic agent for diabetes, was selected as a positive control drug, and administered at a dose of 100 mg/kg. The complex selected as an anti-diabetes and/or anti-obesity effective candidate was administered at a dose of 100 mg/kg to experimental groups of four mice.

Figure 20A:
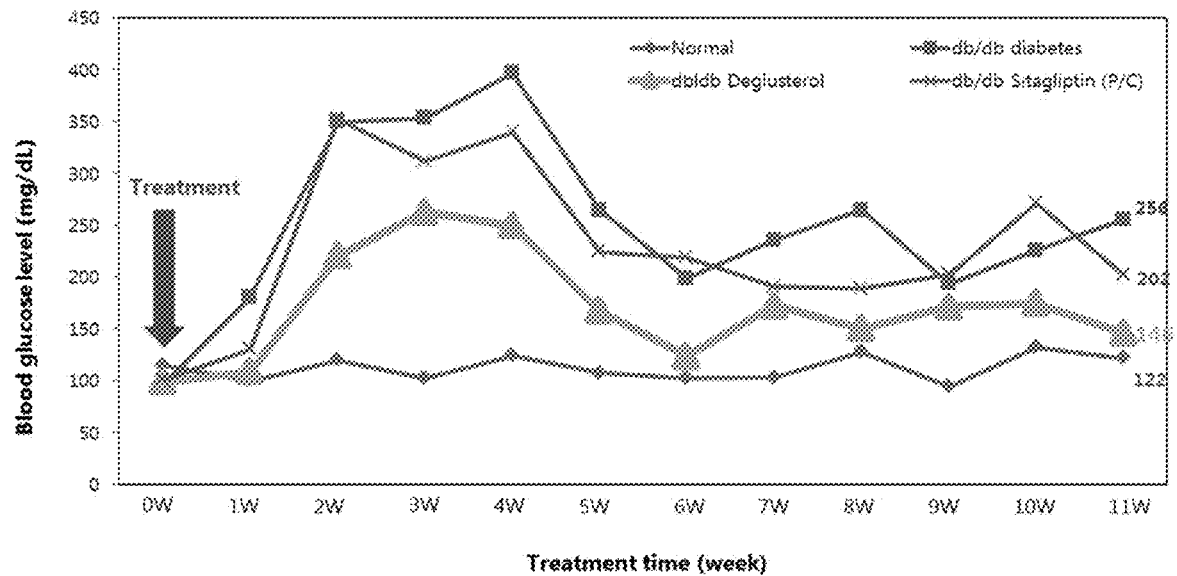
FIG. 20a shows changes in blood sugar level in obesity-induced DB/DB mouse models after treatment with the peptide complex of the present invention.
Figure 20B:
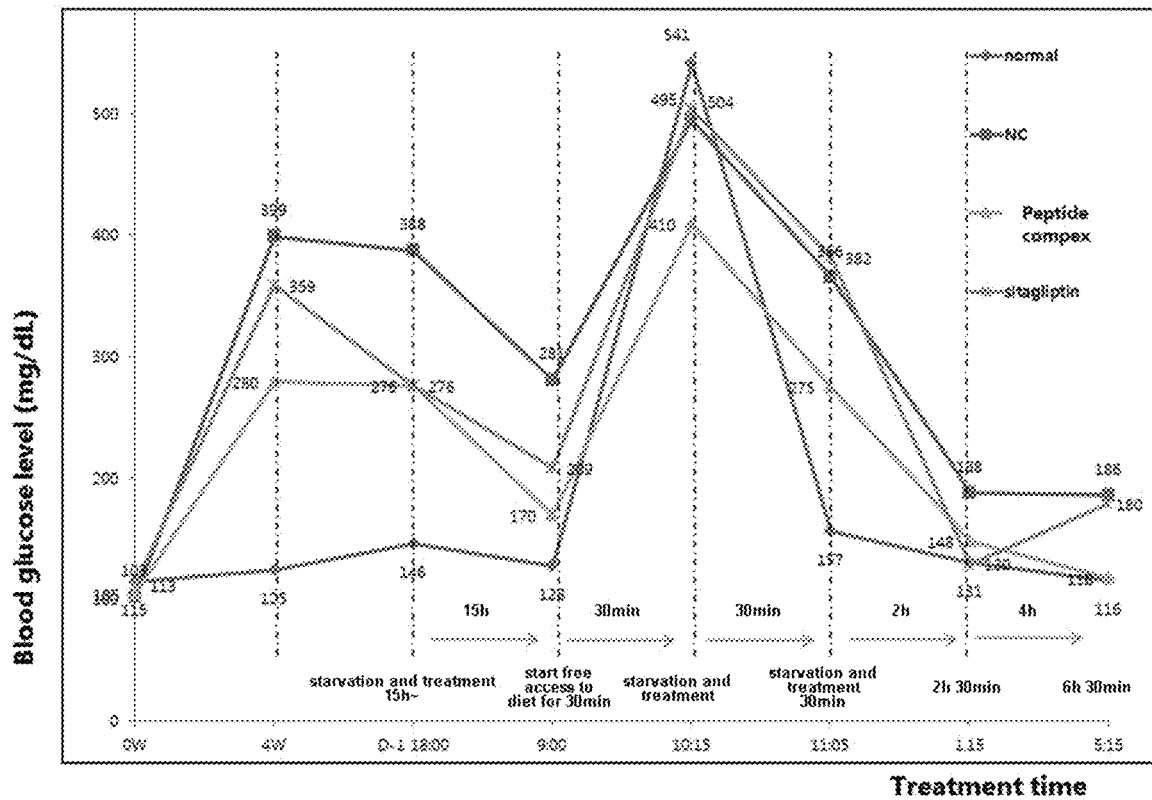
FIG. 20b shows changes in blood sugar level in obesity-induced DB/DB mouse models after treatment with the peptide complex of the present invention.
Figure 21:
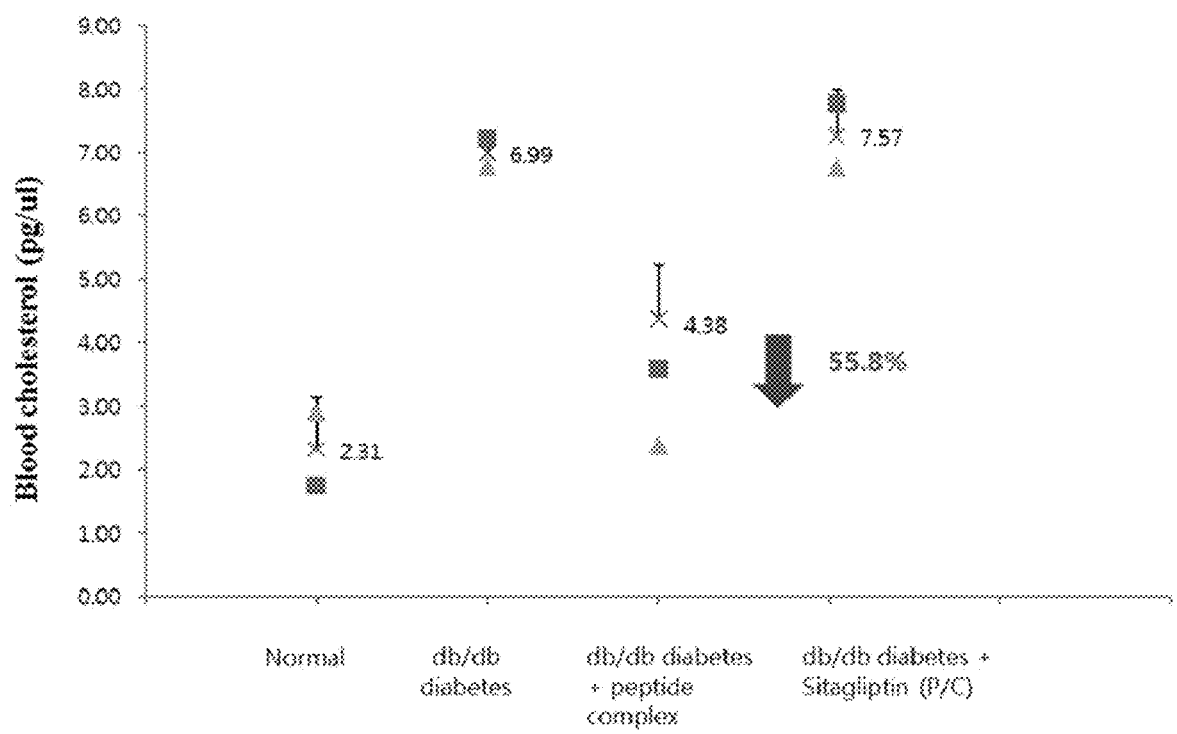
FIG. 21 shows changes in blood cholesterol level in obesity-induced DB/DB mouse models after treatment with the peptide complex of the present invention.

As a result, the peptide complex exhibited a reductive effect on blood sugar levels in which the blood sugar level increased by the high-fat diet was reduced by treatment with the peptide complex. In the diabetes-induced mouse models, the high blood sugar level was decreased by the complex (FIGS. 20a and 20b). Further, lower blood cholesterol levels were detected in the group treated with both the high-fat diet and the peptide complex than the high-fat diet-fed control (FIG. 21).

In addition, after starvation for 16 hours, DB/DB diabetes-induced mice were fed for 30 min and then administered with the peptides. Blood sugar levels were measured over times.

Figure 22A:
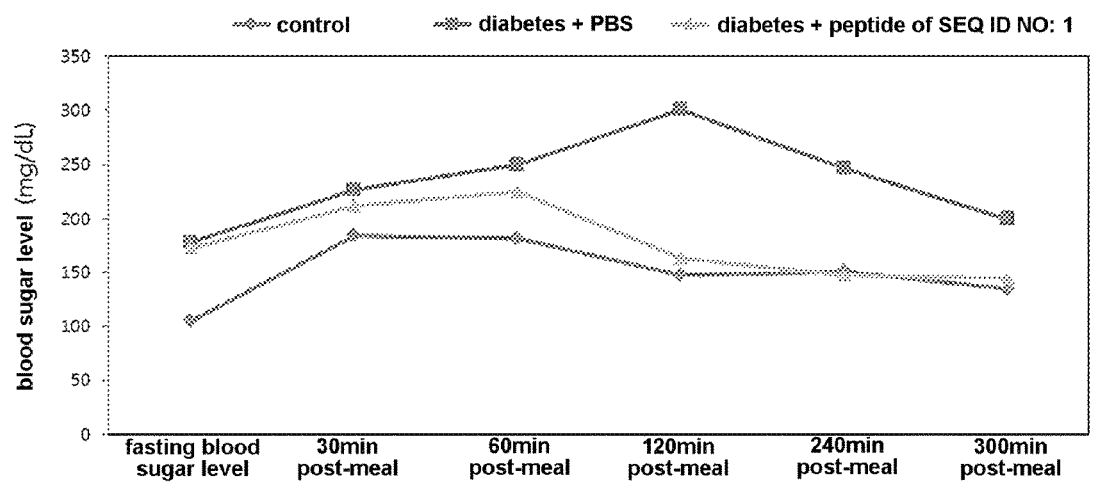
FIG. 22a shows changes in blood sugar level in obesity-induced DB/DB mouse models after treatment with the peptide of SEQ ID NO: 1.

The blood sugar levels in the groups respectively treated with the peptides of SEQ ID NOS: 1, 3, and 5 were observed to decrease in a time-dependent manner (FIGS. 22a-2222c).

Example 5: Promotion of Expression of Insulin and Insulin-like Growth Factor

Promotion of Expression of Insulin and Insulin-like Growth Factor

3T3-L1 cells (pre-adipocytes) were seeded at a density of 3×105 cells/well into 6-well plates and grown for 24 hours. Subsequently, the cells were incubated with various concentrations (10 ng-1 µg/ml) of the peptides for 14 days in a 37° C. incubator. Proteins were extracted from cell lysates which were obtained by treatment with cell lysis buffer, quantitatively analyzed, and subjected to Western blotting using an anti-IGF-1 antibody, which is an antibody against the lipolytic marker, and an insulin antibody (Santa Cruz Biotechnology, USA).

Figure 23:
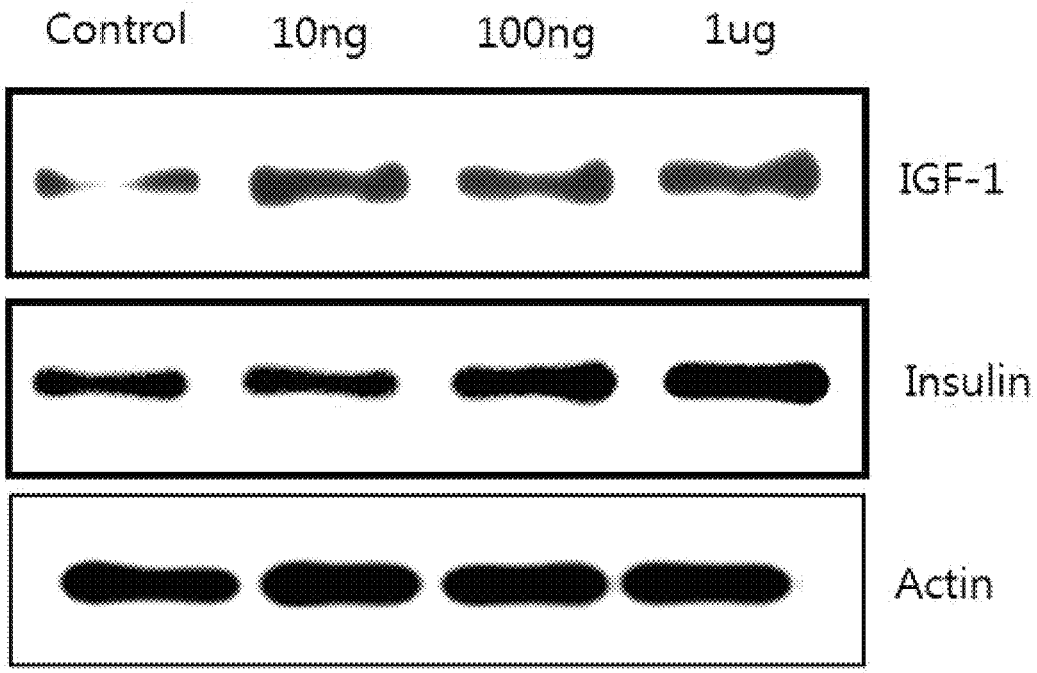
FIG. 23 shows measurement results of expression levels of IGF-1 and insulin after treatment with the peptide of SEQ ID NO: 7.
Figure 24:
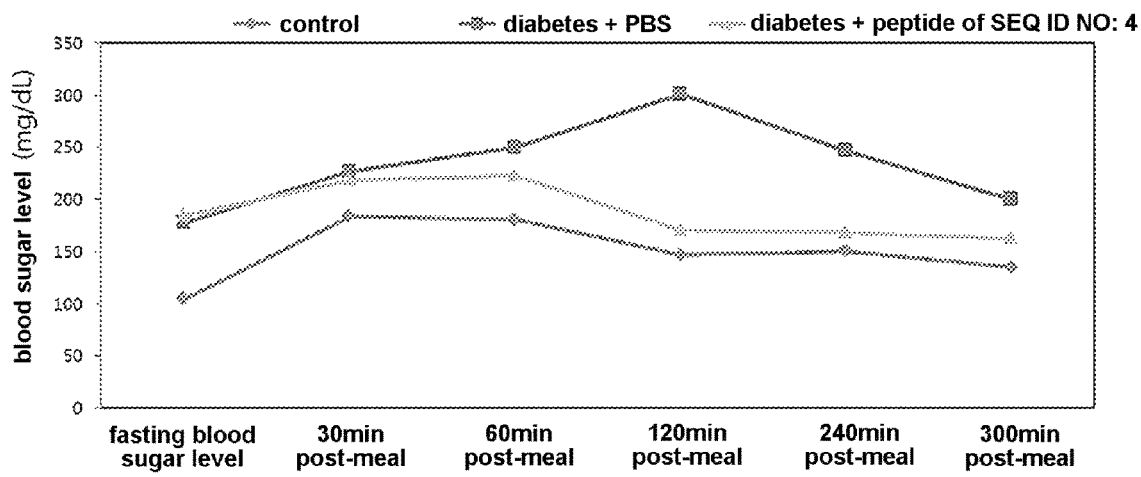
FIG. 24 shows changes in blood sugar level in obesity-induced DB/Db mouse model after treatment with the peptide of SEQ ID NO: 7.
Figure 25A:
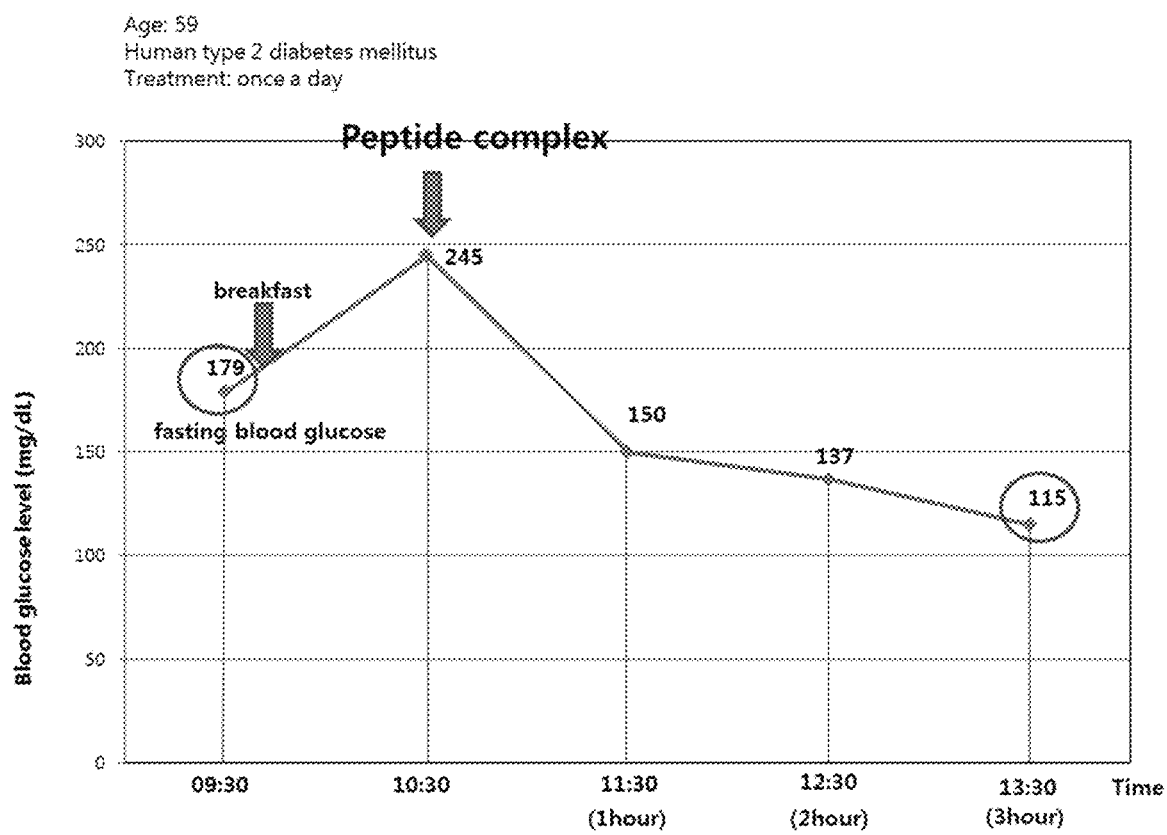
FIG. 25a show changes in blood sugar levels in diabetes patients having high blood glucose levels after treatment with the peptide complex of the present invention.
Figure 25B:
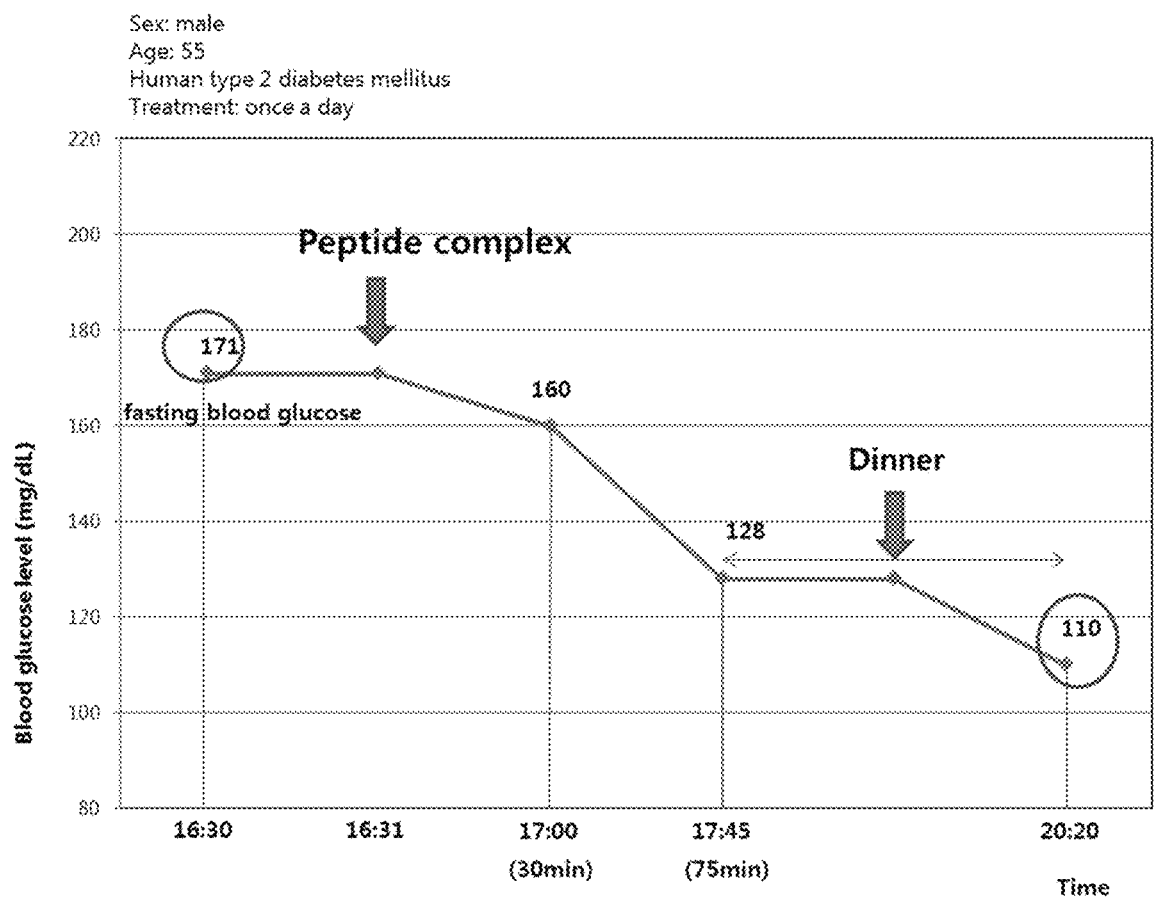
FIG. 25b show changes in blood sugar levels in diabetes patients having high blood glucose levels after treatment with the peptide complex of the present invention.
Figure 25C:
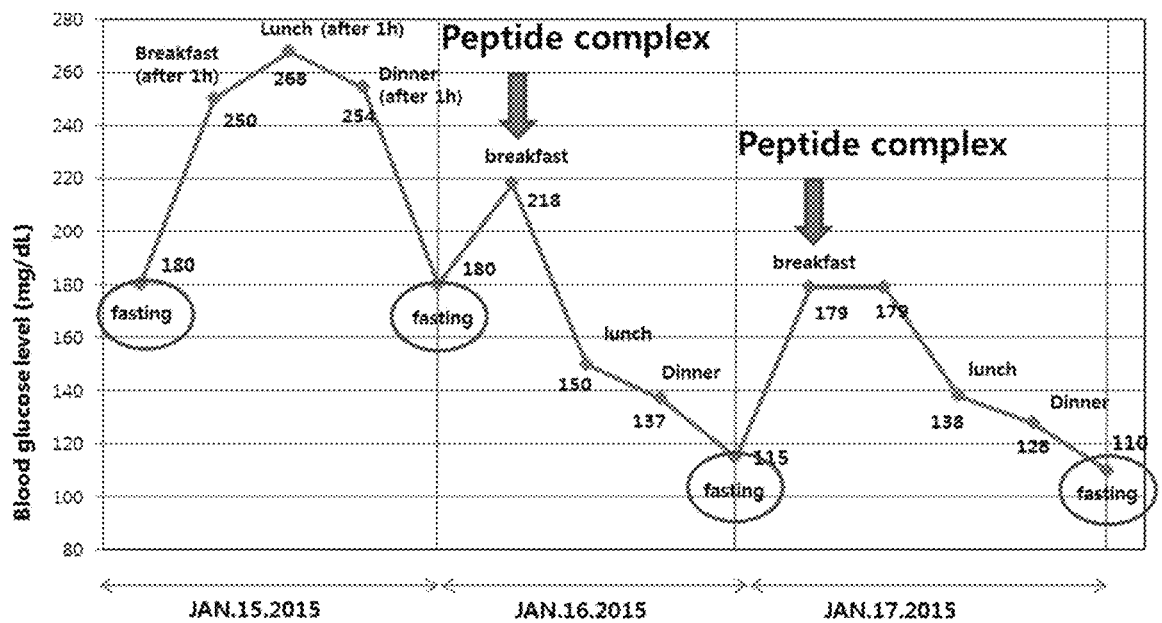
FIG. 25c show changes in blood sugar levels in diabetes patients having high blood glucose levels after treatment with the peptide complex of the present invention.
Figure 25D:
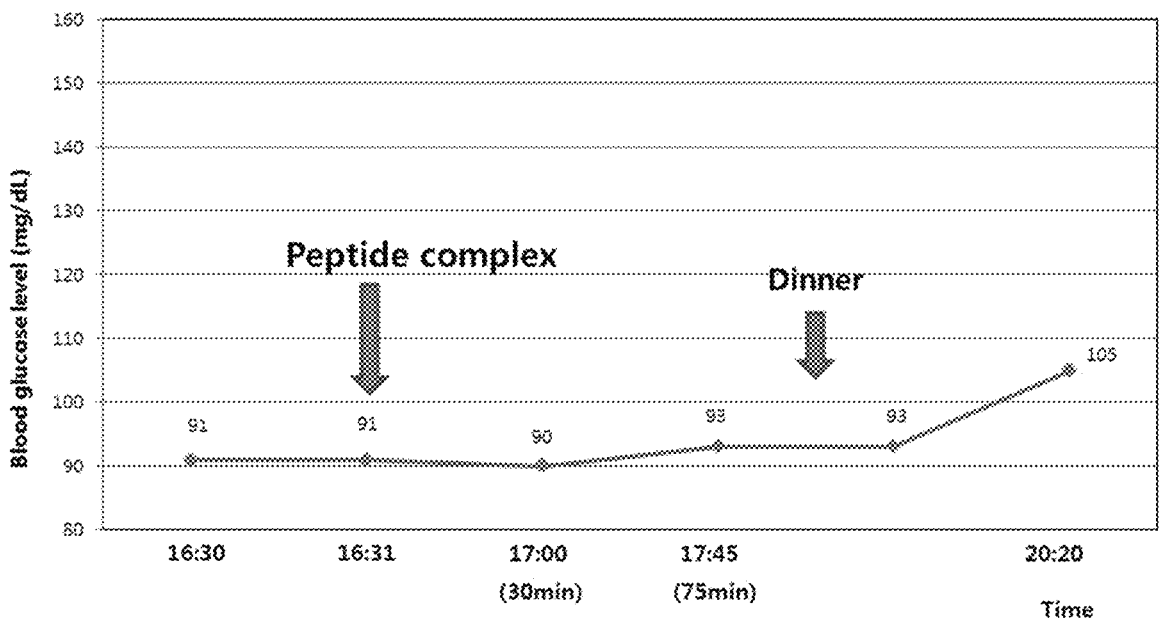
FIG. 25d show changes in blood sugar levels in diabetes patients having high blood glucose levels after treatment with the peptide complex of the present invention.

From the data, it was observed that the peptide of SEQ ID NO: 7 increased the expression of IGF-1 and insulin in dose-dependent manners (FIG. 23).

Example 6: Observation of Blood Sugar Level Reducing Effect in Clinical Experiment Reduction of blood sugar level by intake of the complex.

A brief clinical test was performed on persons 45-65 years old who had a fasting blood glucose level of 170 mg/dL or higher. They were ingested with a complex formulation 30 min after meals. Blood samples were taken at intervals of 30, 60, 90, 120, 150, and 180 min from the persons, and measured for glucose level, using Accu-Chek active (Roche).

A reduction of blood sugar level by the complex formulation was observed in all the tested persons (FIGS. 25a-25d).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

We claim:

1. A peptide consisting of the amino acid sequence of SEQ ID NO: 4 or 5.

2. A peptide consisting of the amino acid sequence of SEQ ID NO: 4 or 5 and exhibiting anti-obesity or anti-diabetes activity.

3. The peptide of claim 2, wherein the peptide suppresses adipogenesis.

4. The peptide of claim 2, wherein the peptide reduces expression of PPARγ(peroxisome proliferator-activated receptor gamma), ACC (acetyl-CoA carboxylase), or aP2 (adipose-specific fatty acid-binding protein 2).

5. The peptide of claim 2, wherein the peptide promotes lipolysis.

6. The peptide of claim 2, wherein the peptide increases expression of pHSL (phospho-hormone-sensitive lipase), AMPK-α1 (AMP-activated protein kinase α1), CGI-58 (comparative gene identification-58), or ATGL (adipose triglyceride lipase).

7. The peptide of claim 2, wherein the peptide reduces a blood sugar level.

8. A pharmaceutical composition, comprising the peptide of claim 2 as an effective ingredient for preventing or treating obesity.

9. A pharmaceutical composition, comprising the peptide of claim 2 as an effective ingredient for preventing or treating Type II diabetes.

10. A method for preventing or treating obesity or Type II diabetes, comprising administering a pharmaceutically effective amount of the peptide of claim 2 into a subject.

* * * * *

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Peptide 1

<400> SEQUENCE: 1

Leu Lys Thr Arg Asn
1               5
```

```
<210> SEQ ID NO 2
<211> LENGTH: 9
<212> TYPE: PRT
<213> ORGANISM: Artificial Sequence
<220> FEATURE:
<223> OTHER INFORMATION: Peptide 2

<400> SEQUENCE: 2

Lys Gly Ala Cys Thr Gly Trp Met Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Peptide 3

<400> SEQUENCE: 3

Lys Gly Ala Ser Thr Gly Trp Met Ala
1               5

<210> SEQ ID NO 4
<211> LENGTH: 10
<212> TYPE: PRT
<213> ORGANISM: Artificial Sequence
<220> FEATURE:
<223> OTHER INFORMATION: Peptide 4

<400> SEQUENCE: 4

Ala Cys Tyr Leu Pro His Pro Trp Phe Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Peptide 5

<400> SEQUENCE: 5

Ala Ser Tyr Leu Pro His Pro Trp Phe Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Peptide 6

<400> SEQUENCE: 6

Cys Asp Leu Arg Arg Leu Glu Met Tyr Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Peptide 7

<400> SEQUENCE: 7

Ser Asp Leu Arg Arg Leu Glu Met Tyr Ser
1               5                   10
```

```
<210> SEQ ID NO 8
<211> LENGTH: 20
<212> TYPE: DNA
<213> ORGANISM: Artificial Sequence
<220> FEATURE:
<223> OTHER INFORMATION: PPARgamma F

<400> SEQUENCE: 8
ttttcaaggg tgccagtttc                                           20

<210> SEQ ID NO 9
<211> LENGTH: 20
<212> TYPE: DNA
<213> ORGANISM: Artificial Sequence
<220> FEATURE:
<223> OTHER INFORMATION: PPARgamma R

<400> SEQUENCE: 9
aatccttggc cctctgagat                                           20

<210> SEQ ID NO 10
<211> LENGTH: 24
<212> TYPE: DNA
<213> ORGANISM: Artificial Sequence
<220> FEATURE:
<223> OTHER INFORMATION: ACC F

<400> SEQUENCE: 10
accttactgc catcccatgt gcta                                      24

<210> SEQ ID NO 11
<211> LENGTH: 24
<212> TYPE: DNA
<213> ORGANISM: Artificial Sequence
<220> FEATURE:
<223> OTHER INFORMATION: ACC R

<400> SEQUENCE: 11
gtgcctgatg atcgcacgaa caaa                                      24

<210> SEQ ID NO 12
<211> LENGTH: 20
<212> TYPE: DNA
<213> ORGANISM: Artificial Sequence
<220> FEATURE:
<223> OTHER INFORMATION: aP2 F

<400> SEQUENCE: 12
catcagcgta aatggggatt                                           20

<210> SEQ ID NO 13
<211> LENGTH: 20
<212> TYPE: DNA
<213> ORGANISM: Artificial Sequence
<220> FEATURE:
<223> OTHER INFORMATION: aP2 R

<400> SEQUENCE: 13
acacattcca ccaccagctt                                           20

<210> SEQ ID NO 14
<211> LENGTH: 24
<212> TYPE: DNA
<213> ORGANISM: Artificial Sequence
<220> FEATURE:
<223> OTHER INFORMATION: AMPK-a1 F
```

```
<400> SEQUENCE: 14
tgaccggaca taaagtggct gtga                                            24

<210> SEQ ID NO 15
<211> LENGTH: 24
<212> TYPE: DNA
<213> ORGANISM: Artificial Sequence
<220> FEATURE:
<223> OTHER INFORMATION: AMPK-α1 R

<400> SEQUENCE: 15
tgatgatgtg agggtgcctg aaca                                            24

<210> SEQ ID NO 16
<211> LENGTH: 24
<212> TYPE: DNA
<213> ORGANISM: Artificial Sequence
<220> FEATURE:
<223> OTHER INFORMATION: CGI58 F

<400> SEQUENCE: 16
tgtgcaggac tcttacttgg cagt                                            24

<210> SEQ ID NO 17
<211> LENGTH: 24
<212> TYPE: DNA
<213> ORGANISM: Artificial Sequence
<220> FEATURE:
<223> OTHER INFORMATION: CGI58 R

<400> SEQUENCE: 17
gtttctttgg gcagaccggt ttct                                            24
```